United States Patent
Ebright et al.

(10) Patent No.: US 7,371,745 B2
(45) Date of Patent: May 13, 2008

(54) BIS-TRANSITION-METAL-CHELATE PROBES

(75) Inventors: Richard H. Ebright, North Brunswick, NJ (US); Yon W. Ebright, North Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 172 days.

(21) Appl. No.: 10/946,786

(22) Filed: Sep. 21, 2004

(65) Prior Publication Data
US 2005/0031545 A1 Feb. 10, 2005

Related U.S. Application Data

(63) Continuation-in-part of application No. 10/665,227, filed on Sep. 17, 2003, now Pat. No. 6,919,333, which is a continuation-in-part of application No. PCT/US02/36180, filed on Nov. 12, 2002.

(60) Provisional application No. 60/410,267, filed on Sep. 13, 2002, provisional application No. 60/367,775, filed on Mar. 28, 2002.

(51) Int. Cl.
*A61K 31/352* (2006.01)
*A61K 31/538* (2006.01)
*C07D 265/28* (2006.01)
*C07D 407/06* (2006.01)

(52) U.S. Cl. ............... 514/229.5; 514/338; 544/64

(58) Field of Classification Search ......... 514/229.5, 514/338; 544/64
See application file for complete search history.

(56) References Cited

FOREIGN PATENT DOCUMENTS

EP     1215501 A1    6/2002

OTHER PUBLICATIONS

Crowe et al., "6xHis-Ni-NTA Chromatography as a Superior Technique in Recombinant Protein Expression/Purification", *Methods in Molecular Biology, Vol. 31: Protocols for Gene Analysis*, A. J. Harwood, ed., pp. 371-387 (1994).
Geoghegan et al., "Site-Directed Conjugation of Nonpeptide Groups to Peptides and Proteins via Periodate Oxidation of a 2-Amino Alcohol. Application to Modification at N-Terminal Serine", *Bioconjugate Chem.*, vol. 3, pp. 138-146 (1992).
Gershon et al., "Stable chelating linkage for reversible immobilization of oligohistidine tagged proteins in the BIAcore surface plasmon resonance detector", *Journal of Immunological Methods*, vol. 183, pp. 65-76 (1995).
Griffin et al., "Specific Covalent Labeling of Recombinant Protein Molecules Inside Live Cells", *Science*, vol. 281, pp. 269-272 (1998).
Hochuli et al., "Genetic Approach to Facilitate Purification of Recombinant Proteins with a Novel Metal Chelate Adsorbent", *Bio/Technology*, pp. 1321-1325 (Nov. 1988).
Hochuli et al., "New Metal Chelate Adsorbent Selective for Proteins and Peptides Containing Neighbouring Histidine Residues", *Journal of Chromatography*, vol. 411, pp. 177-184 (1987).
Jameson, David M. et al., "Fluorescence Anisotropy Applied to Biomolecular Interactions", *Methods in Enzymology*, vol. 246, pp. 283-300 (1995).
Kienberger et al., "Recognition Force Spectroscopy Studies of the NTA-His6 Bond", *Single Mol. 1*, pp. 59-65 (2000).
Muir, Tom W., et al., "Expressed protein ligation: A general method for protein engineering", *Proc. Natl. Acad. Sci. USA*, vol. 95, pp. 6705-6710 (1998).
Nieba et al., "BIACORE Analysis of Histidine-Tagged Proteins Using a Chelating NTA Sensor Chip", *Analytical Biochemistry*, vol. 252, pp. 217-228 (1997).
O'Shannessy et al., "Detection and Quantitation of Hexa-Histidine-Tagged Recombinant Proteins on Western Blots and by a Surface Plasmon Resonance Biosensor Technique", *Analytical Biochemistry*, vol. 229, pp. 119-124 (1995).
Sato, Haruya, et al., "Site-Specific Modification of Interleukin-2 by the Combined Use of Genetic Engineering Techniques and Transglutaminase", *Biochemistry*, vol. 35, pp. 13072-13080 (1996).
Schmitt et al., "A Metal-Chelating Microscopy Tip as a New Toolbox for Single-Molecule Experiments by Atomic Force Microscopy", *Biophysical Journal*, vol. 78, pp. 3275-3285 (2000).
Sulkowski, Eugene, "Purification of proteins by IMAC", *Trends in Biotechnology*, vol. 3, No. 1 (1985).

*Primary Examiner*—Taofiq Solola
(74) *Attorney, Agent, or Firm*—Hoffmann & Baron, LLP

(57) ABSTRACT

A molecule for labeling a target material is provided including two transition-metal chelates and a detectable group. The molecule has the general structural formula (I):

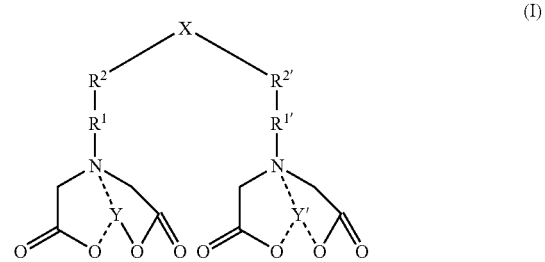

wherein: (a) Y and Y' are each a transition metal, (b) $R^1$ and $R^{1'}$ are each independently $CH(COO^-)$, $CH(COOH)$, or absent; (c) $R^2$ and $R^{2'}$ are linkers each having a length of from about 3.0 to about 20 Å; and (d) X is a detectable group. The linkers may be linear or branched, may contain aromatic moieties, and may optionally be further substituted. Methods of using the molecules of the invention as probes in detecting and analyzing target materials as well as kits including the molecule of the invention are also provided.

20 Claims, 8 Drawing Sheets

SEQUENCE LISTING

<160> NUMBER OF SEQ ID NOS: 9

<210> SEQ ID NO 1
<211> LENGTH: 4
<212> TYPE: PRT
<213> ORGANISM: Artificial Sequence
<220> FEATURE:
<223> OTHER INFORMATION: Target Sequence

<400> SEQUENCE: 1

His His His His
1

<210> SEQ ID NO 2
<211> LENGTH: 5
<212> TYPE: PRT
<213> ORGANISM: Artificial Sequence
<220> FEATURE:
<223> OTHER INFORMATION: Target Sequence

<400> SEQUENCE: 2

His His His His His
1               5

<210> SEQ ID NO 3
<211> LENGTH: 6
<212> TYPE: PRT
<213> ORGANISM: Artificial Sequence
<220> FEATURE:
<223> OTHER INFORMATION: Target Sequence

<400> SEQUENCE: 3

His His His His His His
1               5

<210> SEQ ID NO 4
<211> LENGTH: 7
<212> TYPE: PRT
<213> ORGANISM: Artificial Sequence
<220> FEATURE:
<223> OTHER INFORMATION: Target Sequence

<400> SEQUENCE: 4

His His His His His His His
1               5

<210> SEQ ID NO 5
<211> LENGTH: 8
<212> TYPE: PRT
<213> ORGANISM: Artificial Sequence
<220> FEATURE:
<223> OTHER INFORMATION: Target Sequence

<400> SEQUENCE: 5

His His His His His His His His
1               5

<210> SEQ ID NO 6
<211> LENGTH: 9
<212> TYPE: PRT
<213> ORGANISM: Artificial Sequence
<220> FEATURE:
<223> OTHER INFORMATION: Target Sequence

<400> SEQUENCE: 6

His His His His His His His His His
1               5

<210> SEQ ID NO 7
<211> LENGTH: 10
<212> TYPE: PRT
<213> ORGANISM: Artificial Sequence
<220> FEATURE:
<223> OTHER INFORMATION: Target Sequence

<400> SEQUENCE: 7

```
His His His His His His His His His His
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Target Sequence

<400> SEQUENCE: 8

His His His His His His His His His His His
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Target Sequence

<400> SEQUENCE: 9

His His His His His His His His His His His His
1               5                   10
```

BIS-TRANSITION-METAL-CHELATE PROBES

CROSS REFERENCE TO RELATED APPLICATIONS

This application is a continuation-in-part of application Ser. No. 10/665,227, filed Sep. 17, 2003 now U.S. Pat. No. 6,919,333, which is a continuation-in-part of International Application No. PCT/US02/36180 filed on Nov. 12, 2002, which claims the benefit of U.S Provisional Application No. 60/410,267, filed Sep. 13, 2002 and U.S. Provisional Application No. 60/367,775, filed Mar. 28, 2002, the contents all of which are herein incorporated by reference.

This invention was made with Government support under Grant No. NIH R01-GM41376, awarded by the National Institutes of Health. Therefore, the Government has certain rights in this invention.

FIELD OF THE INVENTION

This invention relates to inventive molecules and methods useful in labeling target molecules. More particularly, the present invention relates to certain transition metal chelate molecules capable of selectively associating with histidine-containing target sequences on target materials or compounds of interest and yielding a detectable signal. The invention further relates to kits for use of the inventive transition metal chelate molecules.

BACKGROUND OF THE INVENTION

Characterization of proteins often requires the ability to incorporate detectable groups—e.g., fluorochromes, chromophores, spin labels, radioisotopes, paramagnetic atoms, heavy atoms, haptens, crosslinking agents, and cleavage agents—at specific, defined sites. For proteins that do not contain pre-existing cysteine residues, site-specific labeling can be accomplished by use of site-directed mutagenesis to introduce a cysteine residue at the site of interest, followed by cysteine-specific chemical modification to incorporate the labeled probe. However, for proteins that contain pre-existing cysteine residues, site-specific labeling is difficult. Multiple strategies have been reported: (i) intein-mediated labeling ("expressed protein ligation"), (Muir, et al., *Proc. Nat'l. Acad. Sci. USA*, 95:6705-6710 (1998)); (ii) trans-glutaminase-mediated labeling (Sato et al., *Biochem.* 35:13072-13080 (1996)); (iii) oxidation-mediated labeling (Geoghegan, et al., *Bioconj. Chem.*, 3:138-146 (1992)); and (iv) trivalent-arsenic-mediated labeling (Griffin et al., *Science* 281:269-272, 1998) (U.S. Pat. No. 6,008,378). Strategies (i)-(iii) do not permit in situ labeling (i.e., direct labeling of proteins in cuvettes, gels, blots, or biological samples—without the need for a subsequent purification step) or in vivo labeling (i.e., direct labeling of proteins in cells). Strategy (iv) requires a structural scaffold presenting two trivalent-arsenic atoms in a precisely defined spatial relationship and therefore relates only to a limited number of detectable groups (such as those having a detectable xanthene, xanthanone, or phenoxazinestructural nucleus).

Transition-metal chelates consisting of a transition-metal ion, such as $Ni^{2+}$, $Co^{2+}$, $Cu^{2+}$, or $Zn^{2+}$, in complex with a tridentate or tetradentate chelating ligand, such as iminodiacetic acid (IDA) or nitrilotriacetic acid (NTA), exhibit high affinity for oligohistidine sequences, particularly hexahistidine sequences (Sulkowski, E., *Trends Biotechnol.*, 3:1-7 (1985); Hochuli, et al., *J. Chromat.* 411:177-184 (1987); Hochuli, E. et al. *BioTechnol.* 6:1321-1325 (1988). FIG. 1 shows a proposed model for binding of a neighboring hexahistidine residue to a Ni-NTA resin as disclosed in Crowe, J. et al., *Methods Mol. Biol.*, 31:371-387 (1994)).

The high affinity of interactions between transition-metal chelates and oligohistidine sequences, particularly hexahistidine sequences, has been verified using force microscopy experiments, which permit direct measurement of interaction forces on the single-molecule level and direct observation of molecular recognition of a single receptor-ligand pair (Kienberger, F. et al. *Single Mol.* 1:59-65 (2000); Schmitt, L. et al. *Biophys. J.* 78: 3275-3285 (2000)).

The high affinity of interactions between transition-metal chelates and oligohistidine sequences, particularly hexahistidine sequences, has been used advantageously to purify biomolecules containing, or modified to contain, "oligohistidine tags," particularly "hexahistidine tags" (Hochuli, E. et al. *BioTechnol.* 6:1321-1325 (1988); Crowe, J. et al., *Methods Mol. Biol.*, 31:371-387 (1994)). In this application, termed "immobilized-metal-chelate affinity chromatography," a transition-metal chelate consisting of a transition-metal ion, such as $Ni^{2+}$, $Co^{2+}$, $Cu^{2+}$, or $Zn^{2+}$, in complex with a tridentate or tetradentate chelating ligand, such as iminodiacetic acid (IDA) or nitrilotriacetic acid (NTA), is immobilized on a solid phase, such as chromatographic resin, and the resulting immobilized metal chelate is used to bind, and thereby purify from other components, tagged biomolecules.

The high affinity of interactions between transition-metal chelates and oligohistidine tags, particularly hexahistidine tags, also has been used advantageously in biosensor analysis of biomolecules containing, or modified to contain, oligohistidine tags, particularly hexahistidine tags (Gershon, et al. *J. Immunol. Meths.* 183:65-76 (1995); Nieba, L. et al. *Anal. Biochem.* 252:217-228 (1997)). Kienberger et al., *Single Mol.* 1; S9-65 (2000). In this application, a transition-metal chelate consisting of a transition-metal ion, such as $Ni^{2+}$, $Co^{2+}$, $Cu^{2+}$, or $Zn^{2+}$, in complex with a tridentate or tetradentate chelating ligand, such as iminodiacetic acid (IDA) or nitrilotriacetic acid (NTA), is immobilized on a biosensor chip, such a surface-plasmon-resonance biosensor chip, and the resulting immobilized metal chelate is used to detect, quantify, and analyze tagged biomolecules.

It would be advantageous to be able to use the high affinity of interactions between transition-metal chelates and oligohistidine tags, particularly hexahistidine tags, in labeling and in situ detection of tagged target materials, in particular, biomolecules.

There is a need for improved methods and compositions for protein labeling. In particular, there is a need for methods and compositions that permit in situ labeling, that permit in vivo labeling, and that encompass a wide range of detectable groups with different properties.

SUMMARY OF THE INVENTION

The invention provides a molecule with two pendant metal-chelate moieties according to the general structural Formula (I), including tautomers, salts, and acids thereof:

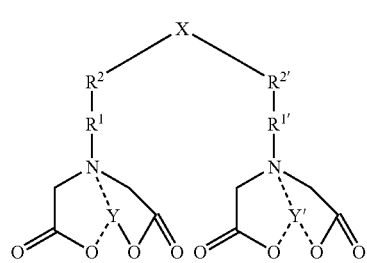

(I)

wherein: (a) Y and Y' are each a transition metal, (b) $R^1$ and $R^{1'}$ are each independently $C(COO^-)$, $CH(COOH)$, or absent; (c) $R^2$ and $R^{2'}$ are linkers each having a length of from about 3.0 to about 20 Å; and (d) X is a detectable group. The linkers may be linear or branched, may contain aromatic moieties, and optionally may be further substituted.

Also provided is a composition including one or more molecules according to Formula (I) and one or more electrophoretic media.

Additionally provided herein are methods of synthesis of compounds of the present invention involving coupling of:
(a) a synthon which includes a bis-activated-ester derivative of a detectable group; and
(b) a synthon which includes an amine or hydrazide derivative of a chelator; and then adding a transition metal.

Additionally provided herein are methods of synthesis of compounds of the present invention containing a non-sulfonated cyanine or squaraine detectable group, involving coupling of: (a) a synthon selected from mono-chelator-functionalized 2,3,3-trimethylindole, mono-chelator-functionalized 2,3,3-trimethylbenzindole, mono-chelator-functionalized 2-methyl-pyridine, mono-chelator-functionalized 2-methyl-benzothiazole, mono-chelator-functionalized 2-methyl-napthothiazole, mono-chelator-functionalized 2-methyl-benzoxazole, and mono-chelator-functionalized 2-methyl-napthoxazole; (b) a synthon, identical or nonidentical to the synthon in (a), selected from the group in (a); and (c) a synthon containing at least one carbon atom; and then adding a transition metal.

Additionally provided herein are methods of synthesis of compounds of the present invention containing a disulfonated cyanine or squaraine detectable group, involving coupling of: (a) a synthon selected from mono-chelator-functionalized 2,3,3-trimethyl-5-sulfanato-indole, mono-chelator-functionalized 2,3,3-trimethyl-6-sulfanato-benzindole, mono-chelator-functionalized 2-methyl-5-sulfanato-pyridine, mono-chelator-functionalized 2-methyl-5-sulfanato-benzothiazole, mono-chelator-functionalized 2-methyl-6-sulfanato-napthothiazole, mono-chelator-functionalized 2-methyl-5-sulfanato-benzoxazole, and mono-chelator-functionalized 2-methyl-6-sulfanato-napthoxazole; (b) a synthon, identical or nonidentical to the synthon in (a), selected from the group in (a); and (c) a synthon containing at least one carbon atom; and then adding a transition metal.

Additionally provided herein are methods of synthesis of compounds of the present invention containing a monosulfonated cyanine or squaraine detectable group, involving coupling of: (a) a synthon selected from mono-chelator-functionalized 2,3,3-trimethylindole, mono-chelator-functionalized 2,3,3-trimethylbenzindole, mono-chelator-functionalized 2-methyl-pyridine, mono-chelator-functionalized 2-methyl-benzothiazole, mono-chelator-functionalized 2-methyl-napthothiazole, mono-chelator-functionalized 2-methyl-benzoxazole, and mono-chelator-functionalized 2-methyl-napthoxazole; (b) a synthon selected from mono-chelator-functionalized 2,3,3-trimethyl-5-sulfanato-indole, mono-chelator-functionalized 2,3,3-trimethyl-6-sulfanato-benzindole, mono-chelator-functionalized 2-methyl-5-sulfanato-pyridine, mono-chelator-functionalized 2-methyl-6-sulfanato-benzothiazole, mono-chelator-functionalized 2-methyl-6-sulfanato-napthothiazole, mono-chelator-functionalized 2-methyl-5-sulfanato-benzoxazole, and mono-chelator-functionalized 2-methyl-6-sulfanato-napthoxazole; and (c) a synthon containing at least one carbon atom; and then adding a transition metal.

Additionally provided herein are methods of synthesis of compounds of the present invention containing a xanthene, xanthanone, or phenoxazine detectable group, involving reaction of a xanthene, xanthanone, or phenoxazine detectable group, a secondary-amine derivative of a chelator, and formaldehyde, according to the Mannich reaction (Mannich, C. et al. Arch. Pharm. 250:647, 1912); followed by addition of a transition metal.

Additionally provided herein is a labeled target material including a target sequence of the form: $(H)_i$, wherein H is histidine, and i is 4 to 12, preferably 4 to 8, and most preferably 6, and wherein the target sequence is bonded with a molecule according to Formula (I).

Also included is a detectable complex including a molecule according to Formula (I) and a target sequence, bonded thereto. The target sequence includes an amino acid sequence of the form: $(H)_i$, wherein H is histidine, and i is 4 to 12, preferably 4 to 8, and most preferably 6.

The invention also includes a method for imparting fluorescent properties to a target material, including the step of reacting: (a) the target material having a target sequence of the form $(H)_i$, wherein H is histidine, and i is 4 to 12, preferably 4 to 8, and most preferably 6, with (b) a molecule according to Formula (I), under conditions sufficient to permit metal-chelate moieties of said molecule according to Formula (I) to bond to the target sequence.

Also provided is a method for detecting one or more molecules that include a target sequence of the form $(H)_i$, wherein H is histidine and i is an integer of from 4 to 12, the method including the steps of: (a) providing a sample including one or more molecules having a target sequence; (b) subjecting the target material to electrophoresis in an electrophoretic medium; (c) contacting the electrophoretic medium with at least one molecule according to Formula (I) having a detectable group under conditions sufficient to permit transition-metal-chelate moieties of the molecule of Formula (I) to associate with the target sequence; and (d) detecting the detectable group, thereby detecting the one or more molecules having a target sequence.

Furthermore, provided herein is a method for detecting a target material of interest, including the steps of: (a) providing a target material of interest having a target sequence of the form: $(H)_i$, wherein H is histidine, and i is 4 to 12, preferably 4 to 8, and most preferably 6; (b) incubating the polypeptide with a molecule according to Formula (I), having a detectable group, for a time period sufficient to allow labeling of the target material; and (c) detecting the detectable group, thereby detecting the target material of interest.

Additionally, a method for imaging the localization, concentration or interactions of a target material of interest on or within cells, tissues, organs or organisms is provided, including the steps of: (a) providing a target material of interest having a target sequence of the form: $(H)_i$, wherein H is histidine, and i is 4 to 12, preferably 4 to 8, and most preferably 6; (b) incubating the target material with a molecule according to Formula (I) for a time period sufficient to allow labeling of the polypeptide; and (c) detecting the detectable group of said molecule according to Formula (I), thereby imaging the localization, concentration or interactions of the target material of interest.

Furthermore, provided herein is an assay method for monitoring a binding process including the steps of: (a) reacting a first component of a specific binding pair with a second component of the pair, with the first component being labeled with a molecule according to Formula (I) having a detectable group; and (b) monitoring the reaction by monitoring a change in a signal of the detectable group.

Also provided herein is an assay method for monitoring a binding process including the steps of: (a) reacting a first component of a specific binding pair with a second component of the pair, with the first component being labeled with a molecule according to Formula (I) having a detectable group; and (b) monitoring the reaction by monitoring fluorescence emission intensity, fluorescence lifetime, fluorescence polarization, fluorescence anisotropy, or fluorescence correlation of the detectable group.

Additionally provided herein is an assay method for monitoring a binding process, including the steps of: (a) reacting a first component of a specific binding pair with a second component of the pair, with the first component being labeled with a molecule according to Formula (I) wherein X of Formula (I) is a fluorochrome, and with the second component containing Y, wherein Y is selected from the group including a fluorochrome and chromophore, Y being capable of participating in fluorescence energy transfer, fluorescence quenching, or exciton formation with X; and (b) monitoring the reaction by monitoring fluorescence of X.

The invention also provides an assay method for monitoring a binding process, including the steps of: (a) reacting a first component of a specific binding pair with a second component of the pair, with the first component being labeled with a molecule according to Formula (I) wherein X of Formula (I) is selected from the group consisting of a fluorochrome and a chromophore, and with the second component containing Y, wherein Y is a fluorochrome able to participate in fluorescence energy transfer, fluorescence quenching, or exciton formation with X; and (b) monitoring the reaction by monitoring fluorescence of Y.

The invention further provides an assay method for monitoring a reaction, including the steps of: (a) reacting a first participant in a reaction with a second participant in the reaction, the first participant being labeled with a molecule according to Formula (I); and (b) monitoring the reaction by monitoring a change in a detectable property of the detectable group.

Furthermore, provided herein is a method for isolating a target material of interest including the steps of: (a) contacting molecules according to Formula (I) immobilized on a solid support, with a solution containing a polypeptide of interest, the polypeptide including a target sequence of the form: $(H)_i$, wherein H is histidine, and i is 4 to 12, preferably 4 to 8, and most preferably 6, under conditions that allow binding of the target material to immobilized molecules of Formula (I); and (b) eluting the target material of interest with a low-molecular weight monothiol or low-molecular-weight dithiol.

The invention also includes a method for immobilizing a target material of interest including the steps of: (a) contacting molecules according to Formula (I) immobilized on a solid support, with a solution containing a target material, the target material containing a target sequence of the form $(H)_i$, wherein H is histidine, and i is 4 to 12, preferably 4 to 8, and most preferably 6, under conditions that allow binding of the target material to immobilized molecules according to Formula (I).

Additionally, a kit for detecting a target compound is provided including one or more containers, wherein at least one of the containers includes one or more molecules according to Formula (I).

Additionally provided herein is a kit including: (a) a molecule according to Formula (I); and (b) a molecule containing a target sequence including an amino acid sequence of the form: $(H)_i$, wherein H is histidine, and i is an integer of from 4 to 12, preferably 4 to 8, and most preferably 6.

Further provided herein is a kit including: (a) a molecule according to Formula (I); and (b) a reagent that promotes the formation of a complex between the molecule according to Formula (I) and a peptide having a target sequence of the form: $(H)_i$, wherein H is histidine, and i is 4 to 12, preferably 4 to 8, and most preferably 6.

Further provided is a kit including one or more containers, having one or more molecules according to Formula (I) therein, the kit further including one or more of: (a) one or more gels; (b) one or more containers including molecules having a target sequence of an amino acid sequence of the form $(H)_i$, wherein H is histidine and i is an integer of from 4 to 12; (c) one or more containers including antibodies having an epitope with an amino acid sequence of the form $(H)_i$, wherein H is histidine and i is an integer of from 4 to 12; (c) one or more containers including one or more denaturing agents; (d) one or more containers including one or more buffer; and (e) one or more sets of instructions.

Further provided is a composition including one or more molecules according to Formula (I) and one or more electrophoretic media.

Also provided is a solution for staining target molecules in an electrophoretic medium, the solution comprising one or more molecules according to Formula (I), wherein the molecules according to Formula (I) are present in a concentration sufficient to stain molecules including a target sequence in an electrophoretic medium, the target sequence including an amino acid sequence of the form $(H)_i$, wherein H is histidine and i is an integer of from 4 to 12.

Additionally, a kit including one or more containers having a stock solution of at least one molecule of Formula (I) is provided.

DETAILED DESCRIPTION OF THE PREFERRED EMBODIMENTS

Figure 1:
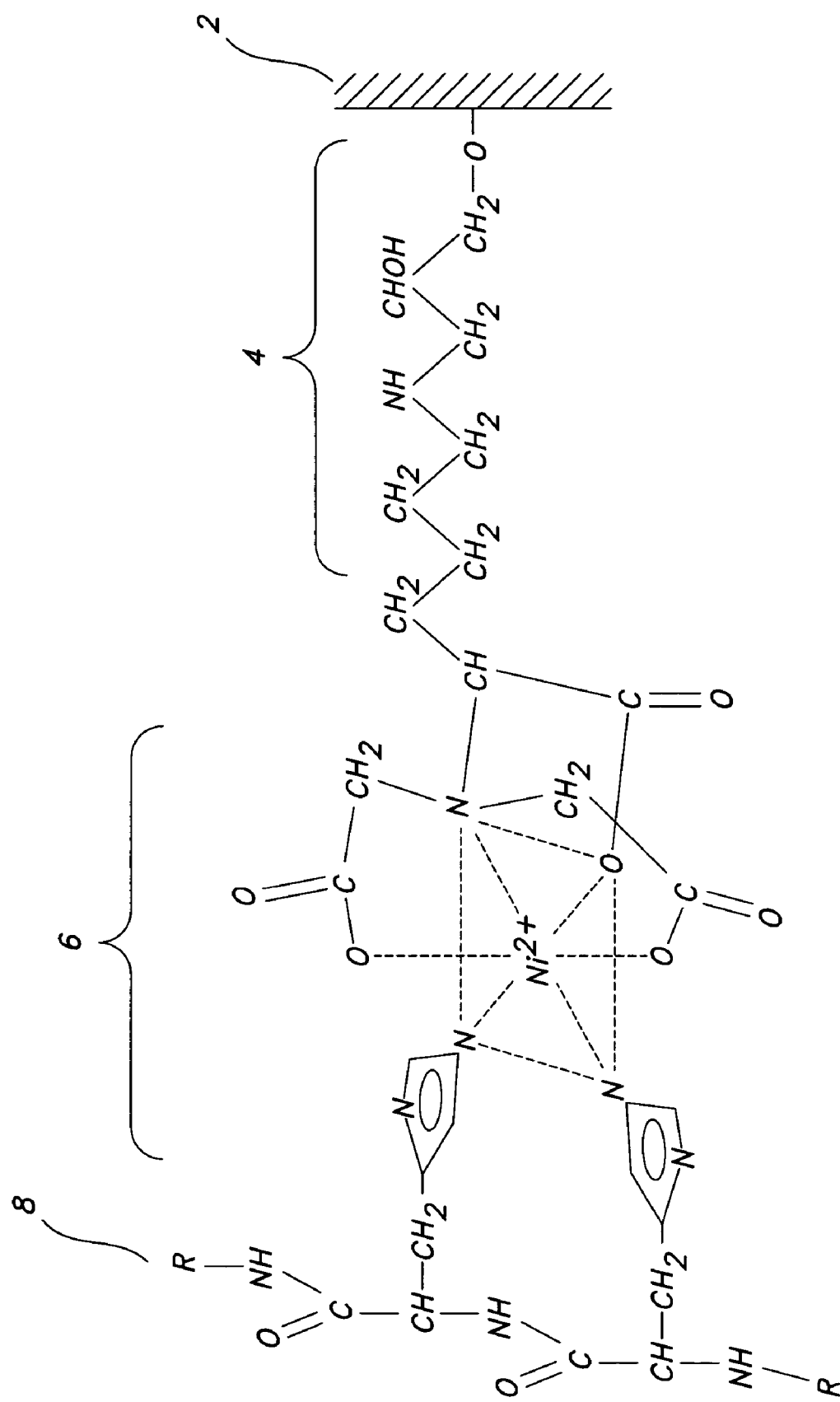
FIG. 1 shows a prior-art model for the binding of neighboring hexahistidine residues to a NTA—$Ni^{2+}$ resin.

The inventors have found, as set forth herein, that a molecule having two transition-metal chelates and a detectable group binds with high affinity and high specificity to oligohistidine target sequences, particularly hexahistidine target sequences.

Furthermore, the inventors have found that a molecule having two transition-metal chelates and a detectable group binds with much higher affinity (more than 10 times higher affinity) and much higher specificity (more than 10 times higher specificity) to oligohistidine target sequences, particularly hexahistidine target sequences, than does a molecule having only a single transition-metal chelate and a detectable group.

Furthermore, the inventors have found that a molecule having two transition-metal chelates and a detectable group can be used to label, detect, and analyze target materials containing, or derivatized to contain, oligohistidine target sequences, particularly hexahistidine target sequences.

Furthermore, the inventors have found that a molecule having two transition-metal chelates and a detectable group can be used for in situ labeling, detection, and analysis of target materials containing, or derivatized to contain, oligohistidine target sequences, particularly hexahistidine target sequences (i.e., direct labeling, detection, and analysis of said target materials—without the need for a subsequent purification step).

Compounds of the Invention

The present invention provides a probe for detecting a target material of interest. The probe is a molecule including two transition-metal chelates and a detectable group, according to the following general structural Formula (I), and tautomers, salts, and acids thereof:

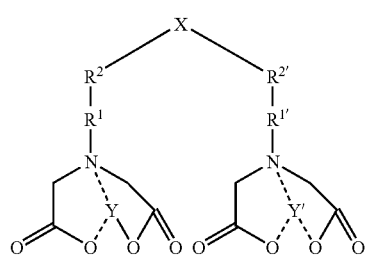

(I)

wherein: (a) Y and Y' are each a transition metal, (b) $R^1$ and $R^{1'}$ are each independently $CH(COO^-)$, $CH(COOH)$, or absent, (c) $R^2$ and $R^{2'}$ are linkers each having a length of about 3.0 to 20 Å, and preferably about 3.0 to 15 Å, and (d) X is a detectable group. The linkers may be linear or branched, may contain aromatic moieties, and may optionally be further substituted.

"Y" in Formula (I) is a transition metal. Y can be any transition metal capable of specific interaction with a oligohistidine tag. Transition metals are those metals having incompletely filled d-orbitals and variable oxidation states. Examples of suitable transition metals include: nickel, cobalt, copper, and zinc. In a preferred embodiment, Y is a divalent transition-metal ion. In a particularly preferred embodiment, Y is selected from the group consisting of $Ni^{2+}$, $Co^{2+}$, $Cu^{2+}$, and $Zn^{2+}$.

When $R^1$ in Formula (I) is absent, the chelator is iminodiacetic acid (IDA). When $R^1$ is $CH(COO—)$ or $CH(COOH)$, the chelator is nitrilotriacetic acid (NTA).

Similarly, when $R^{1'}$ in Formula (I) is absent, the chelator is iminodiacetic acid (IDA). When $R^{1'}$ is $CH(COO—)$ or $CH(COOH)$, the chelator is nitrilotriacetic acid (NTA).

$R^2$ and $R^{2'}$ in Formula (I) are linkers. The structures of $R^2$ and $R^{2'}$ should permit the two pendant transition-metal chelates to be separated by a distance comparable to the dimensions of a oligohistidine target sequence, particularly a hexahistidine target sequence. Thus, the structures of $R^2$ and $R^{2'}$ should permit the two pendant transition-metal chelates to be separated by about 2.5 to 25 Å, and preferably by about 5 to 20 Å (distances measured metal-to-metal). $R^2$ and $R^{2'}$ may be linear or branched, may optionally contain cyclic groups, and may optionally be further substituted. $R^2$ and $R^{2'}$ may be the same or different. Preferably, $R^2$ and $R^{2'}$ are the same. $R^2$ and $R^{2'}$ may be connected to different atoms of X (preferably two atoms on the same edge or face of X). Alternatively, $R^2$ and $R^{2'}$ may be connected to the same atom of X. Alternatively, $R^2$ and $R^{2'}$ may be connected to a single atom, which in turn is connected, directly or through a linker of maximal length 4 Å, to X.

X in Formula (I) is a detectable group. "Detectable group" as used herein refers to any chemical moiety that can be detected. Examples of detectable groups include fluorescent moieties, phosphorescent moieties, luminescent moieties, absorbent moieties, photosensitizers, spin labels, radioisotopes, isotopes detectable by nuclear magnetic resonance, paramagnetic atoms, heavy atoms, haptens, crosslinking agents, cleavage agents, and combinations thereof.

In one embodiment, X is detected by monitoring a signal. Some signals which may be monitored due to the presence of a detectable group include, for example, fluorescence (fluorescence emission intensity, fluorescence lifetime, fluorescence polarization, fluorescence anisotropy, or fluorescence correlation), luminescence, phosphorescence, absorbance, singlet-oxygen production, electron spin resonance, radioactivity, nuclear magnetic resonance, and X-ray scattering.

In another embodiment, X is detected by receptor-binding, protein-protein or protein-nucleic acid crosslinking, or protein or nucleic acid cleavage.

Preferred detectable groups include fluorescent moieties. In one preferred embodiment, cyanine fluorescent moieties are used. These include, but are not limited to: Cy3: 1-R-2-[3-[1-R-1,3-dihydro-3,3-dimethyl-5-sulfo-2H-indol-2-ylidene]-1-propenyl]-3,3-dimethyl-5-sulfo-3H-indolium, Cy5: 1-R-2-[5-[1-R-1,3-dihydro-3,3-dimethyl-5-sulfo-2H-indol-2-ylidene]-1,3-penta dienyl]-3,3-dimethyl-5-sulfo-3H-indolium, Cy7: 1-R-2-[7-[1-R-1,3-dihydro-3,3-dimethyl-5-sulfo-2H-indol-2-ylidene]-1,3,5-heptatrienyl]-3,3-dimethyl-5-sulfo-3H-indolium, indocyanine green and IRDye (1-R-2-[2-[2-R'-3-[(1-R-1,3-dihydro-3,3-dimethyl-5-sulfo-2H-indol-2-ylidene) ethylidene]-1-cyclohexen-1-yl] ethenyl]-3,3-dimethyl-5-sulfo-3H-indolium), and mono- and non-sulfonated derivatives thereof. In another preferred embodiment, squaraine fluorescent moieties are used. In another preferred embodiment, xanthene, xanthanone, and phenoxazine fluorescent moieties are used.

Examples of cyanine, squaraine, xanthene, xanthanone, and phenoxazine detectable groups fluorescent moieties are described, inter alia, in Southwick et al., 1990, *Cytometry* 11:418-430; Mujumdar et al., 1993, *Bioconjugate Chemistry* 4:105-111; Waggoner and Ernst, *Fluorescent Regents for Flow Cytometry*, Part 1: Principles of Clinical Flow Cytometry (1993) and Haugland, *Molecular Probes Handbook of Fluorescent Probes and Research Chemicals*, Molecular Inc. 6th edition (1996) and Berling and Reiser, *Methoden der Organischer Chemie*, p 231-299 (1972), Oswald et al., *Analytical Biochemistry* 280: 272-277 (2000), Oswald et al. *Photochemistry and Photobiology* 74(2): 237-245 (2001), Oswald et al. *Bioconjugate Chemistry* 10: 925-931 (1999), U.S. Pat. No. 6,086,737. The structures in these publications are all incorporated herein by reference.

In a preferred embodiment, X may be selected from the following cyanine detectable groups:

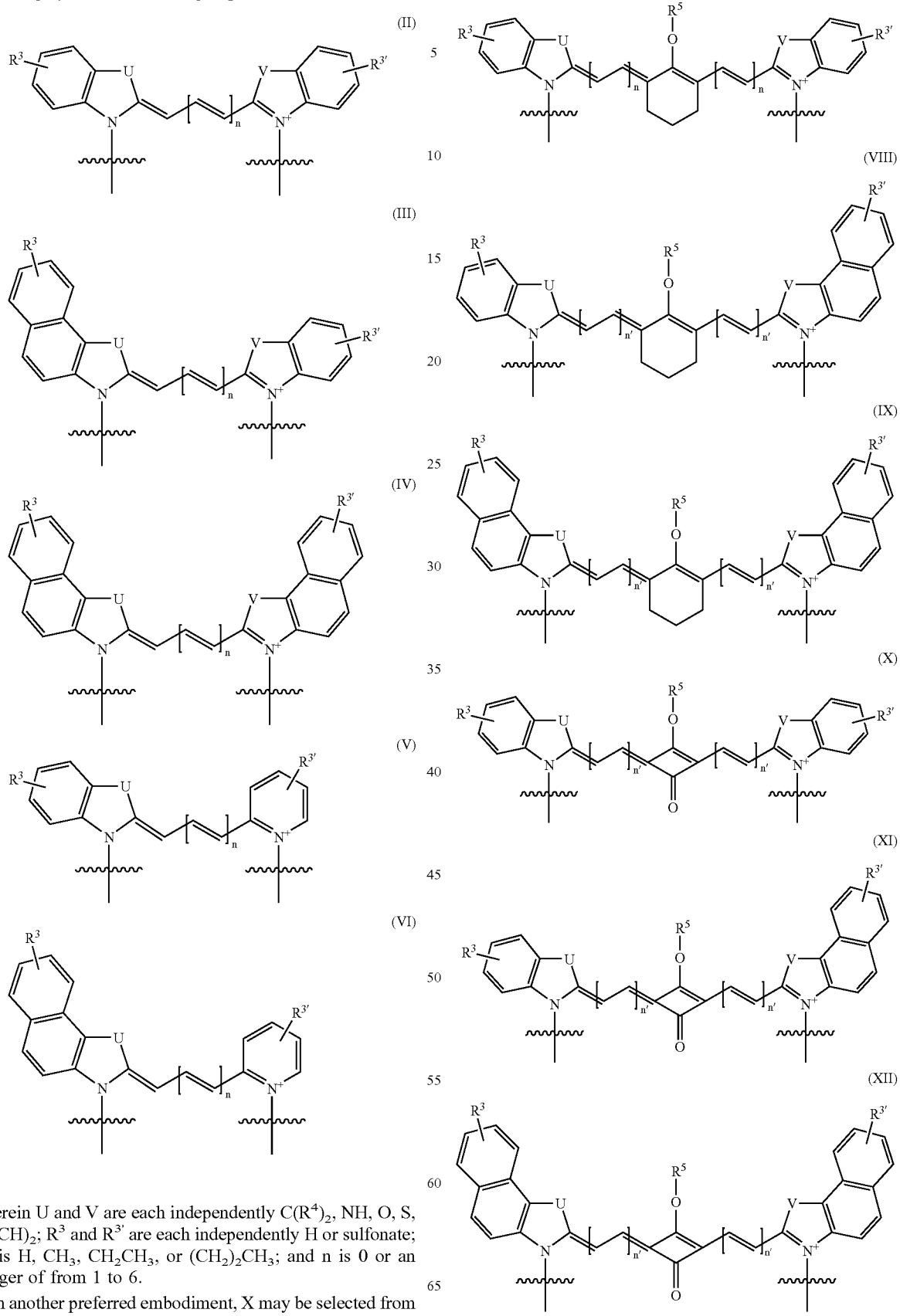

wherein U and V are each independently C(R$^4$)$_2$, NH, O, S, or (CH)$_2$; R$^3$ and R$^{3'}$ are each independently H or sulfonate; R$^4$ is H, CH$_3$, CH$_2$CH$_3$, or (CH$_2$)$_2$CH$_3$; and n is 0 or an integer of from 1 to 6.

In another preferred embodiment, X may be selected from the following squaraine detectable groups:

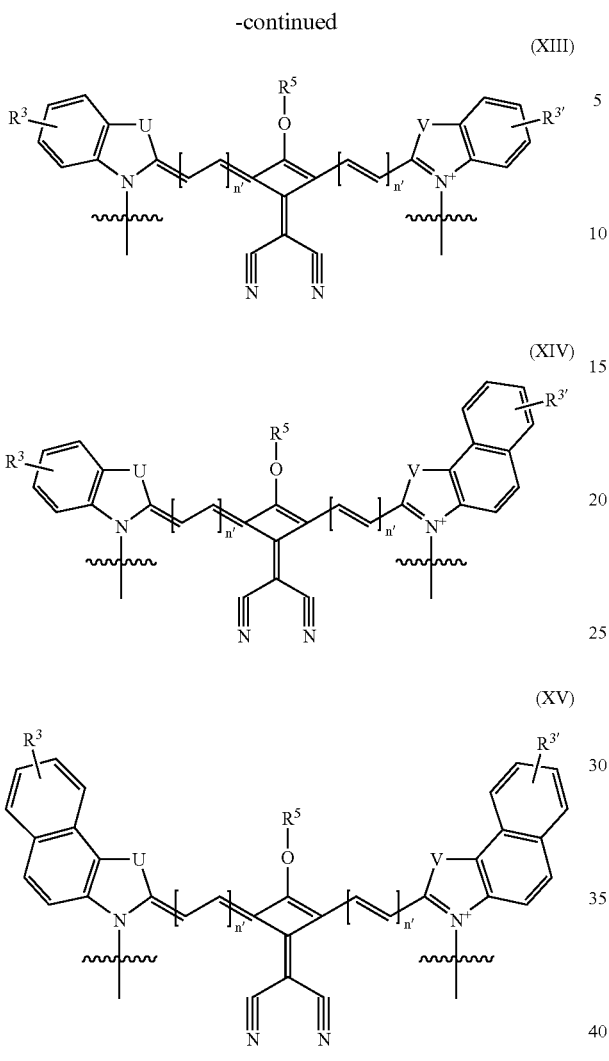

(XIII)

(XIV)

(XV)

wherein U and V are each independently $C(R^4)_2$, NH, O, S, or $(CH)_2$; $R^3$ and $R^{3'}$ are each independently H or sulfonate; $R^4$ is H, $CH_3$, $CH_2CH_3$, or $(CH_2)_2CH_3$; $R^5$ is absent or is selected from the group consisting of H, an alkyl group, and an aryl group; and n' is 0 or an integer of from 1 to 3.

In another preferred embodiment, X may be selected from the following xanthene, xanthanone, and phenoxazine detectable groups:

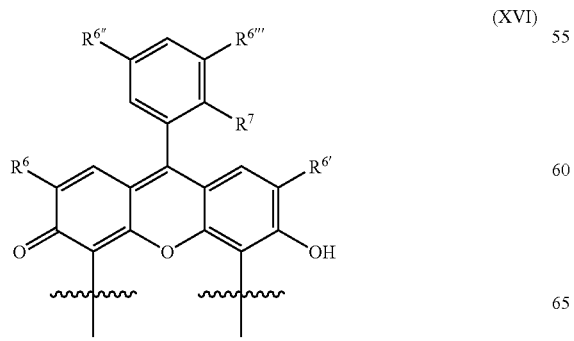

(XVI)

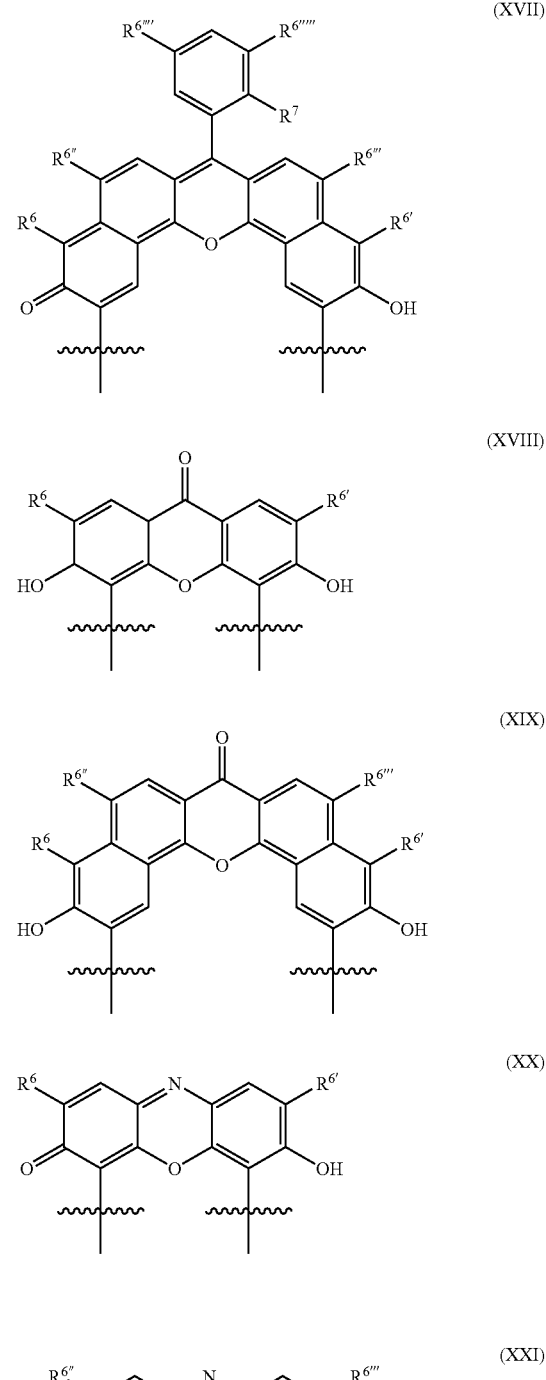

(XVII)

(XVIII)

(XIX)

(XX)

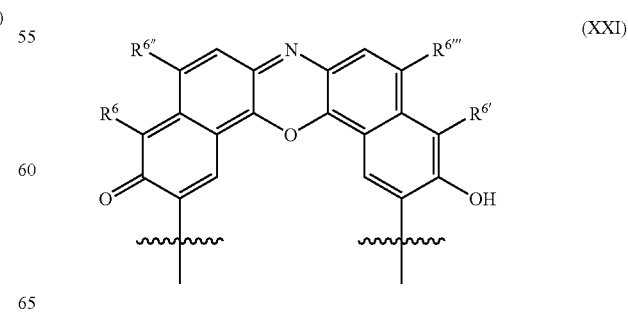

(XXI)

wherein $R^6$, $R^{6'}$, $R^{6''}$, $R^{6'''}$, $R^{6''''}$, and $R^{6'''''}$ are each independently hydrogen, halogen, hydroxyl, or alkoxyl; and $R^7$, when present, is hydrogen, carboxyl, carboxylate or sulfonate.

One preferred molecule of the present invention includes two pendant transition-metal chelates and a cyanine detectable group according to the following general structural formula:

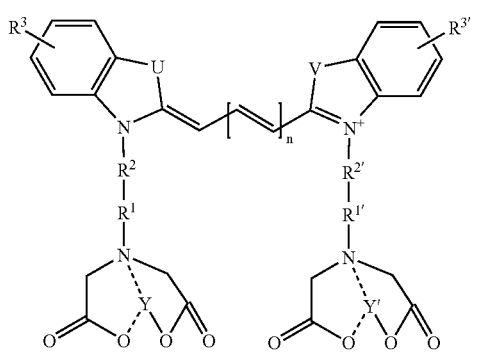

(XXII)

wherein Y, Y', $R^1$, $R^{1'}$, $R^2$, and $R^{2'}$ are as defined previously; wherein U and V are each independently $C(R^4)_2$, NH, O, S, or $(CH)_2$; $R^3$ and $R^{3'}$ are each independently H or sulfonate; $R^4$ is H, $CH_3$, $CH_2CH_3$, or $(CH_2)_2CH_3$; and n is 0 or an integer of from 1 to 6.

Particularly preferred embodiments include the aforementioned structure where n is 1, 2 or 3. In an even more preferred embodiment, n is 1, 2, or 3; and $R^2$ and $R^{2'}$ are identical and are about 3.0 to 15 Å in length. In an especially preferred embodiment, n is 1, 2, or 3; $R^2$ and $R^{2'}$ are identical and about 3.0 to 15 Å in length; and Y and Y' are each $Ni^{2+}$.

One preferred molecule of the present invention includes two pendant transition-metal chelates and a cyanine detectable group according to the following general structural formula:

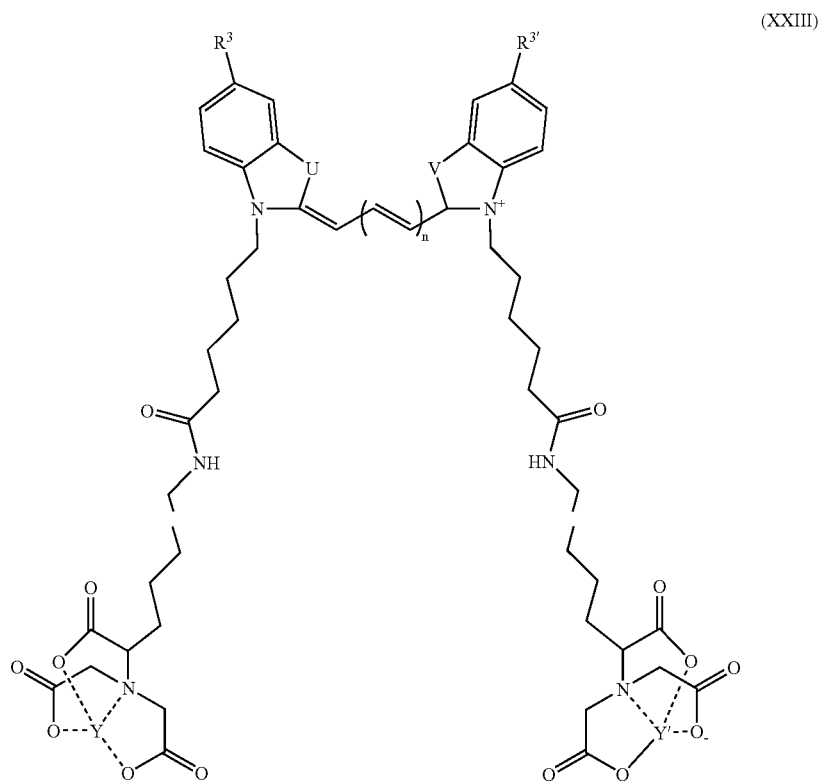

(XXIII)

wherein Y and Y' are as defined previously; U and V are each independently $C(R^4)_2$, NH, O, S, or $(CH)_2$; $R^3$ and $R^{3'}$ are each independently H or sulfonate; $R^4$ is H, $CH_3$, $CH_2CH_3$, or $(CH_2)_2CH_3$; and n is 0 or an integer of from 1 to 6. In a particularly preferred embodiment, n is 1, 2, or 3; and Y and Y' are each $Ni^{2+}$.

Furthermore, provided herein is a molecule with two pendant transition-metal chelates and a detectable group according to the following general structural formula:

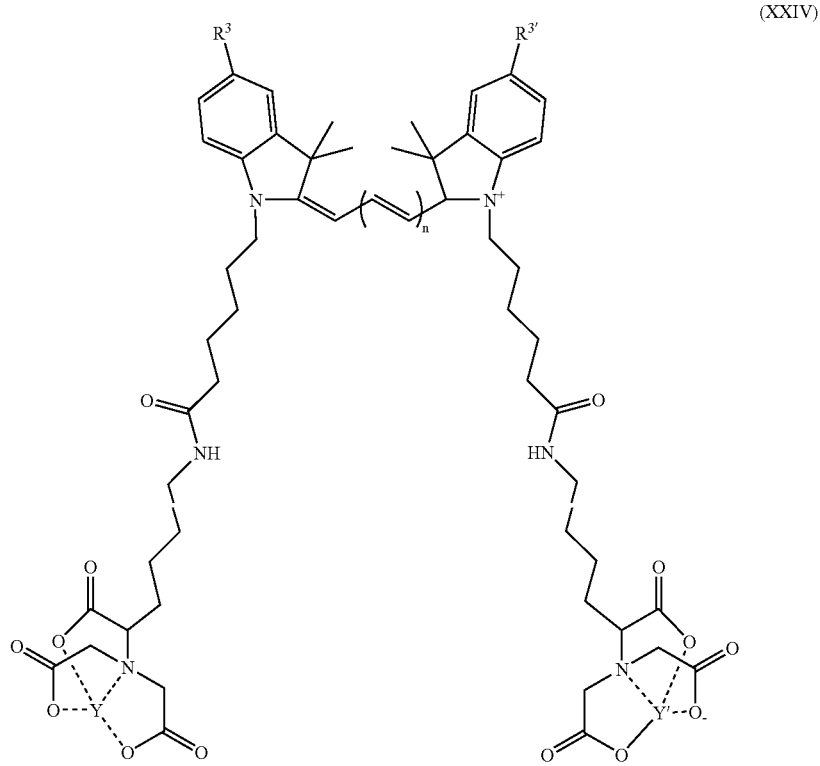

(XXIV)

wherein Y and Y' are as defined previously; $R^3$ and $R^{3'}$ are each independently H or sulfonate; and n is 1, 2, 3, or 4. In a particularly preferred embodiment, n is 1, 2, or 3; and Y and Y' are each $Ni^{2+}$.

There are no particular limitations to the detectable groups of the molecules of the present invention, so long as the ability of the bis-transition-metal-chelate moieties to bind to a target sequence is maintained. The point(s) of attachment between the bis-transition-metal-chelate moieties and the detectable group may vary.

Modifying groups that aid in the use of the bis-transition-metal-chelate molecule may also be incorporated. For example, the bis-transition-metal-chelate molecule may be substituted at one or more positions to add a solid-phase binding group or a crosslinking group.

For applications involving labeling of target materials within cells, the bis-transition-metal-chelate molecule preferably is capable of traversing a biological membrane. Smaller molecules are generally able to traverse a biological membrane better than larger molecules. Bis-transition-metal-chelate molecules of less than 2000 Daltons are preferable for membrane traversal.

The polarity of the bis-transition-metal-chelate molecule can also determine the ability of the bis-transition-metal-chelate molecule to traverse a biological membrane. Generally, a hydrophobic bis-transition-metal-chelate molecule is more likely to traverse a biological membrane. The presence of polar groups can reduce the likelihood of a molecule traversing a biological membrane. A bis-transition-metal-chelate molecule that is unable to traverse a biological membrane may be further derivatized by addition of groups that enable or enhance the ability of the molecule to traverse a biological membrane. Preferably, such derivatization does not significantly alter the ability of the bis-transition-metal-chelate molecule to react subsequently with a target sequence. The bis-transition-metal-chelate molecule may also be derivatized transiently. In such instances, after traversing the membrane, the derivatizing group is eliminated to regenerate the original bis-transition-metal-chelate molecule. Examples of derivatization methods that increase membrane traversability include ether formation with acyloxyalkyl groups. For example, an acetoxymethyl ether is readily cleaved by endogenous mammalian intracellular esterases. Jansen, A. and Russell, T. J., *J. Chem. Soc.*, 2127-2132 (1965). Also, pivaloyl ester is useful in this regard. Madhu et al., *J. Occul. Pharmaco. Ther.*, 14:389-399 (1998).

Methods of Synthesis of Compounds of the Invention

The invention provides methods of synthesis of compounds of the present invention which include coupling of: (a) a synthon which includes a bis-activated-ester derivative of a detectable group; and (b) a synthon which includes an amine or hydrazide derivative of a chelator; and then adding a transition metal.

The invention also provides methods of synthesis of non-sulfonated cyanine or squaraine compounds of the present invention which include coupling of: (a) a synthon selected from mono-chelator-functionalized 2,3,3-trimethylindole, mono-chelator-functionalized 2,3,3-trimethylbenzindole, mono-chelator-functionalized 2-methyl-pyridine, mono-chelator-functionalized 2-methyl-benzothiazole, mono-chelator-functionalized 2-methyl-napthothiazole, mono-chelator-functionalized 2-methyl-benzoxazole, and mono-chelator-functionalized 2-methyl-napthoxazole; (b) a synthon, identical or nonidentical to the synthon in (a), selected from the group in (a); and (c) a synthon containing at least one carbon atom; and then adding a transition metal.

The invention also provides methods of synthesis of disulfonated cyanine or squaraine compounds of the present invention which include coupling of: (a) a synthon selected from mono-chelator-functionalized 2,3,3-trimethyl-5-sulfanato-indole, mono-chelator-functionalized 2,3,3-trimethyl-6-sulfanato-benzindole, mono-chelator-functionalized 2-methyl-5-sulfanato-pyridine, mono-chelator-functionalized 2-methyl-5-sulfanato-benzothiazole, mono-chelator-functionalized 2-methyl-6-sulfanato-napthothiazole, mono-chelator-functionalized 2-methyl-5-sulfanato-benzoxazole, and mono-chelator-functionalized 2-methyl-6-sulfanato-napthoxazole; (b) a synthon, identical or nonidentical to the synthon in (a), selected from the group in (a); and (c) a synthon containing at least one carbon atom; and then adding a transition metal.

The invention also provides methods of synthesis of monosulfonated cyanine or squaraine compounds of the present invention which include coupling of: (a) a synthon selected from mono-chelator-functionalized 2,3,3-trimethylindole, mono-chelator-functionalized 2,3,3-trimethylbenzindole, mono-chelator-functionalized 2-methyl-pyridine, mono-chelator-functionalized 2-methyl-benzothiazole, mono-chelator-functionalized 2-methyl-napthothiazole, mono-chelator-functionalized 2-methyl-benzoxazole, and mono-chelator-functionalized 2-methyl-napthoxazole; (b) a synthon selected from mono-chelator-functionalized 2,3,3-trimethyl-5-sulfanato-indole, mono-chelator-functionalized 2,3,3-trimethyl-6-sulfanato-benzindole, mono-chelator-functionalized 2-methyl-5-sulfanato-pyridine, mono-chelator-functionalized 2-methyl-6-sulfanato-benzothiazole, mono-chelator-functionalized 2-methyl-6-sulfanato-napthothiazole, mono-chelator-functionalized 2-methyl-5-sulfanato-benzoxazole, and mono-chelator-functionalized 2-methyl-6-sulfanato-napthoxazole; and (c) a synthon containing at least one carbon atom; and then adding a transition metal.

Coupling of the synthons referred to herein can be accomplished in a single step, or in two steps. For example, for symmetric compounds (i.e., where (a) and (b) are identical), coupling of the reactants (a), (b), and (c) desirably is carried out in a single step. For asymmetric compounds (i.e., where (a) and (b) are non-identical), coupling of the reactants (a), (b), and (c) desirably is carried out in two steps: i.e., reaction of (a) with (c), followed by reaction of the resultant product with (c); or, alternatively, reaction of (b) with (c), followed by reaction of the resultant product with (a).

Coupling of the synthons referred to herein can be performed in solution, or with one or more synthons attached to a solid support.

Coupling of the synthons referred to herein can be performed with the chelator in an unprotected form, or with the chelator in a protected form initially and deprotected thereafter.

The invention also provides methods of synthesis of xanthene, xanthanone, or phenoxazine compounds of the present invention which include reaction of a xanthene, xanthanone, or phenoxazine detectable group, a secondary-amine derivative of a chelator, and formaldehyde, according to the Mannich reaction. See, Mannich, C. et al. *Arch. Pharm.* 250:647, (1912), the entirety of which is herein incorporated by reference. This reaction is followed by the addition of a transition metal.

The Mannich reaction referred to herein can be performed with the chelator in an unprotected form, or with the chelator in a protected form initially and deprotected thereafter.

Target Materials and Target Sequences of the Invention

The invention provides detectable complexes of molecules according to Formula (I) with target sequences. Detectable complexes as used herein refer to the association between target amino acid sequences and bis-transition-metal-chelate molecules according to the invention.

Suitable target materials include, but are not limited to, polypeptides, and polypeptide mimetics (such as peptide nucleic acid). Preferably, the target material is a polypeptide.

As used herein, "polypeptide" refers to both short chains, commonly referred to as "peptides," "oligopeptides," or "oligomers," and to longer chains, generally referred to as "proteins". Polypeptides may contain amino acids other than the 20 gene-encoded amino acids. Polypeptides may include amino acid sequences modified either by natural processes, such as post-translational processing, or by chemical modification techniques which are well-known in the art. Such modifications are well described in basic texts and in more detailed monographs, as well as in research literature. Thus "polypeptide" includes peptides, oligopeptides, polypeptides and proteins, all of which terms are used interchangeably herein.

The target material contains, or is modified to contain, at least one copy of an oligohistidine target sequence, herein referred to interchangeably as the "target sequence" or "tag". The target sequence is generally of the form: $(H)_i$, wherein H is histidine and i is an integer of from 4 to 12 (i.e., SEQ ID NOS. 1-9), preferably 4 to 8, and most preferably 6.

The target sequence may be incorporated at any desired site, or set of sites, within a target material, but preferably is incorporated at a site that is (a) accessible and (b) not essential for structure and function of the target material.

For example, when the target material is a protein, the target sequence preferably is incorporated at the N-terminal region, at the C-terminal region, at an internal loop region, at a surface-exposed non-essential loop, at an internal linker region, or at combinations thereof. The specific site, or set of sites, can be chosen to accommodate the functional requirements of a protein. For example, it is known that N-terminal modification of chemokines can affect their activity; therefore, in applications with chemokines, either C-terminal modification or internal modification would be preferable. Since labeling is performed at defined, user-selected sites, effects on the activity of target material can be avoided. When it is important to preserve the activity of the tagged target material, specific activity testing of the tagged vs. the untagged target material may be conducted to verify activity. See, for example, Mas et al,. *Science,* 233:788-790 (1986).

Target-sequence-containing polypeptides may be generated by total synthesis, partial synthesis, in vitro translation, or in vivo bacterial, archaeal, or eukaryotic production.

In one preferred embodiment, the target sequences and/or target-sequence-containing polypeptides used in the invention are prepared using solid-phase synthesis (see, e.g., Merrifield et al. *J. Am. Chem. Soc.,* 85:2149, (1962) Steward and Young, *Solid Phase Peptides Synthesis*, Freeman, San Francisco, (1969), and Chan and White, *Fmoc Solid Phase Peptide Synthesis—A Practical Approach*, Oxford Press (2000)).

In another preferred embodiment, the target sequences and/or target-sequence-containing polypeptides used in the invention are prepared using native chemical ligation (Dawson et al., *Science,* 266:776, 1994).

In an especially preferred embodiment, the target sequences and/or target-sequence-containing polypeptides are generated by in vivo bacterial, archaeal, or eukaryotic expression of a recombinant nucleic acid sequence encoding the target-sequence-containing polypeptide. Methods for the construction of recombinant nucleic acid sequences encoding a tag-containing polypeptide are well known in the art (Sambrook and Russel, *Molecular Cloning A Laboratory Manual*, 3$^{rd}$ Ed., Cold Spring Harbor Laboratory, New York (2001), the entirety of which is herein incorporated by reference). In addition, techniques for transient or stable introduction of recombinant nucleic acid sequences into cells (see, for example, Ausubel et al., *Current Protocols In Molecular Biology*, John Wiley & Sons, Inc. (1995)), for replacement of native nucleic acid sequences by recombinant nucleic acid sequences in cells (see, for example, Ausubel et al., *Current Protocols In Molecular Biology*, John Wiley & Sons, Inc. (1995)), and for expression of recombinant nucleic acid sequences in cells (see e.g., Lee and Arthans, H. J. *Biol. Chem.*, 263:3521, (1988); Rosenberg, et al., *Gene*, 56:125 (1987)), are well known in the art.

The bis-transition-metal-chelate moieties of the molecules according to Formula (I) bind to the oligohistidine target sequence. The transition metals of the bis-transition-metal-chelate moieties bind to imidazole groups of histidines of the oligohistidine target sequence.

Although not intending to be limited to such interpretation, it is believed that the affinity of the bis-transition-metal-chelate molecules for oligohistidine target sequences relates to the presence of two tridentate (where $R^1$ or $R^{1'}$ is absent) or tetradentate (where $R^1$ or $R^{1'}$ is $CH(COO^-)$ or $CH(COOH)$) transition-metal chelates, each having a transition metal with at least two coordination sites available for interaction with electron-donor groups. Oligohistidine target sequences comprising 4 to 12 histidine residues have appropriate electron-donor functionality, size, and flexibility to interact with available coordination sites of the bis-transition-metal-chelate probe, creating a stable linkage therewith.

An example of a transition-metal-chelate molecule of the invention in association with a oligohistidine target sequence, in this case a hexahistidine target sequence, is depicted as follows:

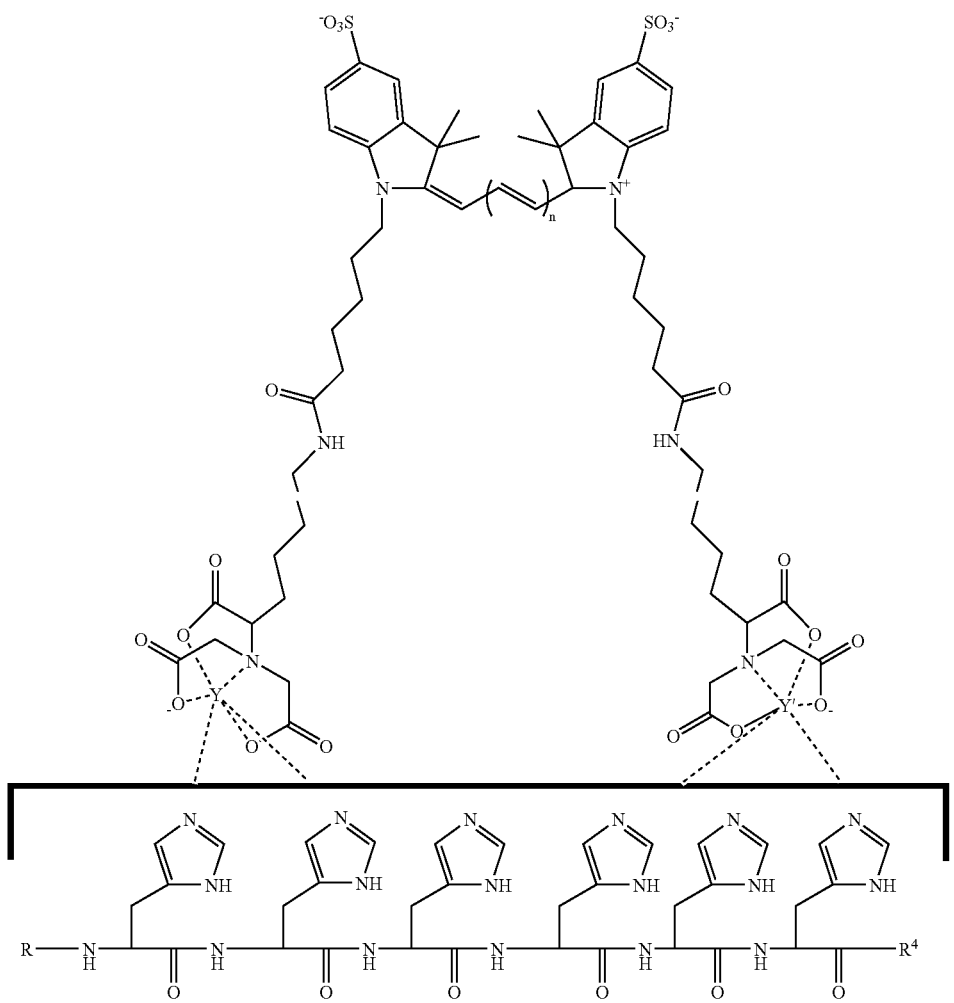

Labeling is accomplished by contacting a bis-transition-metal-chelate molecule according to Formula (I) with a target-sequence-containing target material. The bis-transition-metal-chelate molecule may be contacted with a target-sequence-containing target material located in, for example, a test tube, a microtiter-plate well, a cuvette, a flow cell, or a capillary, or immobilized on, for example a surface or other solid support. Alternatively, the bis-transition-metal-chelate molecule may be contacted with a target-sequence-containing target material located within a cell, tissue, organ, or organism (in which embodiment, the bis-transition-metal-chelate molecule preferably is capable of traversing an intact biological membrane).

In one embodiment, the bis-transition-metal-chelate molecules according to Formula (I) are used to label target-sequence-containing molecules within cells. The bis-transition-metal-chelate molecules of this invention may be introduced into cells by diffusion (for bis-transition-metal-chelate molecules capable of traversing biological membranes) or by microinjection, electroporation, or vesicle fusion (for any bis-transition-metal-chelate molecule). The target-sequence-containing molecules may be introduced into cells by microinjection, electroporation, or vesicle fusion, or by expression of recombinant genes in situ.

In one preferred embodiment, a target-sequence-containing protein produced by expression of a recombinant gene within cells is contacted with a molecule according to Formula (I) by incubating cells in medium containing the molecule. Following labeling, and optionally following further manipulations, cells are imaged using an epi-illumination, confocal, or total-internal-reflection optical microscope with an optical detector, such as a CCD camera, an intensified CCD camera, a photodiode, or a photomultiplier tube, and fluorescence signals are analyzed.

Uses of the Compounds of the Invention

It is contemplated that bis-transition-metal-chelate molecules of the invention may be used in a variety of in vitro and in vivo applications.

Desirably, the molecules of the invention will be used in separation and identification method such as electrophoresis. Electrophoresis is a preparative and/or analytical method used to separate and characterize macromolecules. It is based on the principle that charged particles migrate in an applied electrical field. If electrophoresis is carried out in solution, molecules are separated according to their surface net charge density. If carried out in semisolid materials (gels), however, the matrix of the gel adds a sieving effect so that particles migrate according to both charge and size. The particles separated in this fashion may be stained by exposure to a sufficient concentration of molecules according to Formula (I) so as to render the particles, preferably biomolecules, detectable via a UV detector.

In general, electrophoresis gels can be either in a slab gel or tube gel form. For slab gels, the apparatus used to prepare them, is often referred to as a cassette and usually consists of two glass or plastic plates with a space disposed between them by means of a spacer or gasket material and the apparatus is held together by a clamping means so that the space created is closed on three sides and open at the top. A solution of unpolymerized gel is poured into the space while in its liquid state. A means of creating wells or depressions in the top of the gel (such as a comb) in which to place samples is then placed in the space. The gel is then polymerized and becomes solid. After polymerization is complete, the comb device is removed and the gel, while still held within the plates, is then ready for use. Examples of such apparatus are well known and are described in U.S. Pat. No. 4,337,131 to Vesterberg; U.S. Pat. No. 4,339,327 to Tyler; U.S. Pat. No. 3,980,540 to Hoefer et al.; U.S. Pat. No. 4,142,960 to Hahn et al.; U.S. Pat. No. 4,560,459 to Hoefer; and U.S. Pat. No. 4,574,040 to Delony et al. Tube gels are produced in a similar manner, however, instead of glass or plastic plates, glass capillary tubing is used to contain the liquid gel.

Protein electrophoresis can performed in the presence of a charged detergent like sodium dodecyl sulfate (SDS) which coats the surface of, and thus equalizes the surface charge of, most proteins, so that migration depends on size (molecular weight). Proteins are often separated in this fashion, i.e., SDS-PAGE (PAGE=polyacrylamide gel electrophoresis). One or more denaturing agents, such as urea, can also be included in order to minimize the effects of secondary and tertiary structure on the electrophoretic mobility of proteins. Such additives are typically not necessary for nucleic acids, which have a similar surface charge irrespective of their size and whose secondary structures are generally broken up by the heating of the gel that happens during electrophoresis.

Two commonly used electrophoretic media for gel electrophoresis and other separation techniques are agarose and polyacrylamide. Each of these is described in turn as follows. In standard PAGE technology, gels commonly range between about 5% to about 22.5% T (T=total amount of acrylamide or other gelling agent), mostly between about 7.5% and about 15% T. Lower percentages may be employed with linear polyacrylamide. In agarose gel electrophoresis, concentrations between about 0.2% and about 2% T may be employed.

Agarose is a colloidal extract prepared from seaweed. Different species of seaweed are used to prepare agarose; commercially available agarose is typically prepared from genera including, but not limited to, Gracilaria, Gelidium, and Pterocladia. It is a linear polysaccharide (average molecular mass of about 12,000) made up of the basic repeating unit agarobiose, which comprises alternating units of galactose and 3,6-anhydrogalactose. Agarose contains no charged groups and is thus useful as a medium for electrophoresis.

Agarose gels have very large "pore" size and are used primarily to separate large molecules, e.g., those with a molecular mass greater than about 200 kilodaltons (kD). Agarose gels can be prepared, electrophoresed ("run") and processed faster than polyacrylamide gels, but their resolution is generally inferior. For example, for some macromolecules, the bands formed in agarose gels are "fuzzy" (diffuse). The concentration of agarose typically used in gel electrophoresisis is between from about 1% to about 3%.

Agarose gels are formed by suspending dry agarose in an aqueous, usually buffered, media, and boiling the mixture until a clear solution forms. This is poured into a cassette and allowed to cool to room temperature to form a rigid gel.

Acrylamide polymers are used in a wide variety of chromatographic and electrophoretic techniques and are used in capillary electrophoresis. Polyacrylamide is well suited for size fractionation of charged macromolecules such as proteins and nucleic acids (e.g., deoxyribonucleic acids (DNA), and ribonucleic acids, (RNA)).

The creation of the polyacrylamide matrix is based upon the polymerization of acrylamide in the presence of a crosslinker, usually methylenebisacrylamide (bis, or MBA). Upon the introduction of catalyst, the polymerization of acrylamide and methylene bisacrylamide proceeds via a free-radical mechanism. The most common system of catalytic initiation involves the production of free oxygen radicals by ammonium persulfate (APS) in the presence of the tertiary aliphatic amine N,N,N',N'-tetramethylethylenediamine (TEMED). Various other chemical polymerization systems may be used. For example, TEMED and persulfate may be added to provide polymerization initiation. If desired, an acrylamide gradient may be developed by successively adding solutions with increasing amounts of acrylamide and/or cross-linking agent. Alternatively, differential initiation may be used, so as to provide varying degrees of polymerization and thus prepare a gradient gel.

Electrophoretic gels based on polyacrylamide are produced by co-polymerization of monoolefinic monomers with di- or polyolefinic monomers. The co-polymerization with di- or polyfunctional monomers results in cross-linking of the polymer chains and thereby the formation of the polymer network. Monoolefinic monomers include, by way of non-limiting example, acrylamide, methacrylamide and derivatives thereof such as alkyl-, or hydroxyalkyl derivates, e.g., N-hydroxymethylacrylamide, N,N-dimethylacrylamide, N-hydroxypropylacrylamide. The di- or polyolefinic monomer is preferably a compound containing two or more acryl or methacryl groups such as e.g. methylenebisacrylamide, N,N'-diallyltartardiamide, N,N'-1,2-dihydroxyethylene-bisacrylamide, N,N-bisacrylyl cystamine, trisacryloylhexahydrotriazine. In a broader sense, polyacrylamide also includes gels in which the monoolefinic monomer is selected from acrylic- and methacrylic acid derivatives, e.g., alkyl esters such as ethyl acrylate and hydroxyalkyl esters such as 2-hydroxyethyl methacrylate, and in which cross-linking has been brought about by means of a compound as mentioned before. Further examples of gels based on polyacrylamide are gels made by co-polymerization of acrylamide with a polysaccharide substituted to contain vinyl groups such as allyl glycidyl dextran (see EP 0 087 995).

One type of electrophoresis is usually referred to as isoelectric focusing (IEF) or electrofocusing. IEF, which can be carried out in an electrophoretic medium such as a gel or a a solution, involves passing a mixture through a separation medium which contains, or which may be made to contain, a pH gradient or other pH function. The electrophoretic medium has a relatively low pH at one end, while at the other end it has a higher pH. IEF is discussed in various texts such as *Isoelectric Focusing* by P. G. Righetti and J. W. Drysdale (North Holland Publ., Amsterdam, and American Elsevier Publ., New York, 1976).

IEF is based on the fact that the charge on a molecule, such as a protein, depends on the pH of the ambient solution. At a pH that is equal to the isoelectric point (pI) of a specific molecule, the net charge on that molecule is zero. At a pH above its pI, the molecule has a negative charge, while at a pH below its pI the molecule has a positive charge. When a mixture of molecules is electrophoresed in an IEF system, an anode (positively charged) is placed at the acidic end of the system, and a cathode (negatively charged) is placed at the basic (alkaline) end. Each molecule having a net positive charge under the acidic conditions near the anode will be driven away from the anode. As it moves through the IEF system, the molecule will move through zones that are increasingly less acid, and its positive charge will decrease. Similarly, molecules having a net positive charge under the basic conditions near the cathode will move away from the cathode, and will move through zones that are increasingly less basic. Regardless of its initial starting point, each molecule will stop moving when it reaches its particular isoelectric point, since it no longer has any net charge at that particular pH. This process thus separates molecules having different pI values. The separated molecules can be removed from the IEF medium or from solution by various means, or they can be stained or otherwise characterized without further manipulation. For example, a gel produced by IEF can be fixed and stained in order to detect proteins without removing them from the gel.

Some types of IEF systems generate pH gradients by means of synthetic ampholytes (molecules having both acidic and basic characteristics) that typically have some amount of buffering capacity. Such molecules are known generally as "carrier ampholytes". When placed in an IEF device, each carrier ampholyte will seek its own isoelectric point. Because of their buffering capacity, many carrier ampholytes will establish a pH plateau rather than a single point. By using a proper mixture of carrier ampholytes, it is possible to generate a relatively smooth pH gradient for a limited period of time. Such mixtures are sold commercially under various trade names, such as Ampholine™ and Pharmalyte™ (Amersham Biosciences AB, Uppsala, Sweden), SERVALYT® (SERVA Electrophoresis GmbH, Heidelberg, Germany), and Bio-Lyte (BioRad Laboratories, Hercules, Calif.). The chemistry and synthesis of ampholytes and ampholyte mixtures is discussed in various references, such as U.S. Pat. No. 3,485,736, U.S. Pat. No. 4,131,534, U.S. Pat. No. 5,173,160, U.S. Pat. No. 5,322,906, and U.S. Pat. No. 5,428,116; Matsui et al., Methods Mol. Biol. 112:211-219 (1999); and Lopez, Methods Mol. Biol. 112:109-110 (1999).

In IEF in Immobilized pH gradients (IPG), amphoretic ions are forced to reach a steady-state position along pH inclines of various scopes and spans (see Righetti et al., *Electrophoresis* 15:1040-1043, 1994; Righetti et al., *Methods Enzymol.* 270:235-255, 1996; and *2-D Electrophoresis using immobilized pH gradients—Principles and Methods*, Edition A C, Berkelman, T. and T. Stenstedt, Amersham Biosciences, Freiburg, Germany, 1998.). In one popular version of IPG, the pH gradient is in the form of a strip and is referred to as a "gel strip" or "strip gel" that can be used in appropriate formats. See, by way of non-limiting example, published PCT patent applications WO 98/57161 A1, WO 02/09220 A1, published U.S. patent application US 2003/0015426 A1, and U.S. Pat. Nos. 6,599,410; 6,156,182; 6,113,766; and 6,495,017.

Two dimensional (2D) electrophoresis techniques are also known, involving a first electrophoretic separation in a first dimension, followed by a second electrophoretic separation in a second, transverse dimension. In the 2D method most commonly used, proteins are subjected to IEF in a polyacrylamide gel in the first dimension, resulting in separation on the basis of isolectric point, and are then subjected to SDS-PAGE in the second dimension, resulting in further separation on the basis of size (O'Farrell, *J. Biol. Chem.* 250:4007-4021, 1975).

Capillary zone electrophoresis (CZE) is a technique which permits rapid and efficient separations of charged substances (for a review, see Dolnik, *Electrophoresis* 18:2353-2361, 1997). In general, CZE involves introduction of a sample into a capillary tube, i.e., a tube having an internal diameter from about 5 to about 2000 microns, and the application of an electric field to the tube. The electric potential of the field both pulls the sample through the tube and separates it into its constituent parts. Each constituent of the sample has its own individual electrophoretic mobility; those having greater mobility travel through the capillary tube faster than those with slower mobility. As a result, the constituents of the sample are resolved into discrete zones in the capillary tube during their migration through the tube. An on-line detector can be used to continuously monitor the separation and provide data as to the various constituents based upon the discrete zones.

CZE can be generally separated into two categories based upon the contents of the capillary columns. In "gel" CZE, the capillary tube is filled with a suitable gel, e.g., polyacrylamide gel. Separation of the constituents in the sample is predicated in part by the size and charge of the constituents traveling through the gel matrix. This technique, sometimes referred at as capillary gel electrophoresis (CGE), is reviewed by Kemp (*Biotechnol. Appl. Biochem.* 27:9, 1998). CGE is suitable for resolving macromolecules that differ in size but have a constant charge-to-mass ratio (Guttman et al., *Anal. Chem.* 62:137, 1990).

In "open" CZE, the capillary tube is filled with an electrically conductive buffer solution. Upon ionization of the capillary, the negatively charged capillary wall will attract a layer of positive ions from the buffer. As these ions flow towards the cathode, under the influence of the electrical potential, the bulk solution (the buffer solution and the sample being analyzed), must also flow in this direction to maintain electroneutrality. This electroendosmatic flow provides a fixed velocity component which drives both neutral species and ionic species, regardless of charge, towards the cathode. Fused silica is principally utilized as the material for the capillary tube because it can withstand the relatively high voltage used in CZE, and because the inner walls of a fused silica capillary ionize to create the negative charge which causes the desired electroendosomatic flow. The inner wall of the capillaries used in CZE can be either coated or uncoated. The coatings used are varied and known to those in the art. Generally, such coatings are utilized in order to reduce adsorption of the charged constituent species to the charged inner wall. Similarly, uncoated columns can be used. In order to prevent such adsorption, the pH of the running buffer, or the components within the buffer, are manipulated.

The electrophoretic modalities of the invention can be carried out in any suitable format, e.g., in standard-sized gels, minigels, strips, gels designed for use with microtiter plates and other high throughput (HTS) applications, and the like. Minigel and other formats include without limitation those described in the following patents and published patent applications: U.S. Pat. No. 5,578,180, to Engelhom et al., entitled "System for pH-Neutral Longlife Electrophoresis Gel"; U.S. Pat. Nos. 5,922,185; 6,059,948; 6,096,182; 6,143,154; 6,162,338, all to Updyke et al.; published U.S. Patent Application Nos. 20030127330 A1 and 20030121784 A1; and published PCT Application WO 95/27197, all entitled "System for pH-Neutral Stable Electrophoresis Gel"; U.S. Pat. No. 6,057,106, to Updyke et al., and published PCT application WO 99/37813, both entitled "Sample Buffer and Methods for High Resolution Gel Electrophoresis of Denatured Nucleic Acids"; U.S. Pat. No. 6,562,213 to Cabilly et al., and published PCT application WO 02/18901, both entitled "Electrophoresis Apparatus for Simultaneous Loading of Multiple Samples"; and Published U.S. Patent Application 2002/0134680 A1, to Cabilly et al., and published PCT application WO 02/071024, both entitled "Apparatus and Method for Electrophoresis".

Any suitable buffer can be used to practice the electrophoretic modalities of the invention. Non-limiting examples of buffers include those described herein and in the preceding patents and published patent applications, as well as those described in Righetti et al., *Electrophoresis* 15:1040-1043 (1994); Chiari et al., *Appl. Theor. Electrophor.* 1:99-102 (1989); and Chiari et al., *Appl. Theor. Electrophor.* 1:103-107 (1989). In a particularly preferred embodiment, the buffer provided in a stock solution for use with an electrophoretic gel application will be the same as the loading buffer in the gel.

The bis-transition-metal-chelate molecules of the invention may be used in numerous standard assay formats, as are well known in the art. Some examples of assay formats include fluorescence emission intensity, fluorescence polarization (FP), fluorescence anisotropy (FA), fluorescence resonance energy transfer (FRET), fluorescence correlation spectroscopy (FCS), fluorescence-activated cell—or particle—sorting (FACS), x/y-fluorescence scanning (FluorImaging), epi-illumination optical microscopy, confocal optical microscopy, total-internal-reflection optical microscopy, absorbance spectroscopy, enzyme-linked immunosorbent assay (ELISA), radioimmunoassay (RIA), scintillation proximity assay (SPA), autoradiography, and assays formats that involve use of biotin or other hapten incorporation to provide a recognition event for binding or immobilization of one or more components.

Some further examples, which are intended to be illustrative and not limiting of possible assay formats and applications that could use site specific bis-transition-metal-chelate-labeled target materials, are set forth below.

For example, the bis-transition-metal-chelate molecules of the present invention may be used to detect and/or quantify a polypeptide of interest containing, or derivatized to contain, a target sequence. The target-sequence-containing polypeptide is incubated with a molecule according to Formula (I) for a time period sufficient to allow labeling thereof. Labeled target-sequence-containing polypeptide optionally may be separated from unbound material before the detection step using any method known in the art, and the detectable group X is detected, thereby detecting the polypeptide of interest. The target-sequence-containing polypeptide may be included in any material, including, but not limited to, cuvettes, microtiter plates, capillaries, flow cells, test tubes, gels, blots, and biological samples.

The invention also provides an assay method for monitoring a binding process. In this method, a first component of a specific reaction pair is labeled with a molecule according to Formula (I) and is reacted with a second component of the pair. The reaction can be monitored by monitoring a change in a signal of the detectable group X.

Examples of specific reaction pairs include, but are not restricted to, antibodies/antigens, hormone/receptor, enzyme/substrate, and protein/analyte.

In a fluorescence-emission-intensity assay, the sample is exposed to light of a first wavelength (able to be absorbed by a fluorescent moiety), and fluorescence-emission intensity is monitored at a second wavelength (emitted by said fluorescent moiety). Fluorescence-emission intensity is dependent on the quantity of the fluorescent moiety and on the local environment of the fluorescent moiety.

A fluorescence-emission-intensity assay to detect and quantify binding between two molecules, molecule 1 and molecule 2, may be configured as follows: a reaction mixture is prepared by combining molecule 1 labeled with fluorescent moiety X according to the current invention and molecule 2. Complex formation results, directly or indirectly, from a change in the local environment of X, and, correspondingly, in a change in the fluorescence emission intensity of X. The progress of the reaction is monitored by observing the change in fluorescence emission intensity of X. Equilibrium association and dissociation constants may be extracted from the concentration-dependence of the reaction.

In a fluorescence-polarization (FP) or fluorescence-anisotropy (FA) assay, a sample is exposed to polarized light of a first wavelength (able to be absorbed by a fluorescent moiety), and fluorescence-emission polarization or anisotropy is monitored at a second wavelength (emitted by said fluorescent moiety). Fluorescence-emission polarization or anisotropy is inversely related to the rotational dynamics, and thus to the size, of said fluorescent moiety (or, if said fluorescent moiety is attached to a molecule or complex, to the rotational dynamics, and thus to the size, of the molecule or complex). FP or FA assays permit detection of reactions that result in changes in size of molecules or complexes, including especially, macromolecule-association and macromolecule-dissociation reactions.

An FP or FA assay to detect and quantify binding between two molecules, molecule 1 and molecule 2, may be configured as follows: a reaction mixture is prepared by combining molecule 1 labeled with fluorochrome X according to the current invention and molecule 2. Complex formation results in formation of a higher-molecular-weight, higher-FP, higher-FA species. The progress of the reaction is monitored by observing the decrease in FP or FA. Equilibrium association and dissociation constants are extracted from the concentration-dependence of the reaction.

A further FP or FA assay may be used to detect and quantify proteolytic activity and may be configured as follows: a reaction mixture is prepared by combining a substrate molecule labeled with fluorochrome X according to the present invention and a sample containing a proteolytic enzyme. Cleavage of the substrate molecule by the proteolytic enzyme results in the production of lower-molecular-weight, lower-FP, lower-FA fragments. The progress of the reaction is monitored by observing the decrease in FP or FA.

Fluorescence resonance energy transfer (FRET) is a physical phenomenon that permits measurement of distance). FRET occurs in a system having a fluorescent probe serving as a donor and a second fluorescent probe serving as an acceptor, where the emission spectrum of the donor overlaps the excitation spectrum of the acceptor. In such a system, upon excitation of the donor with light of the donor excitation wavelength, energy can be transferred from the donor to the acceptor, resulting in excitation of the acceptor and emission at the acceptor emission wavelength. FRET readily can be detected—and the efficiency of FRET readily can be quantified—by exciting with light of the donor excitation wavelength and monitoring emission of the donor, emission of the acceptor, or both. The efficiency of energy transfer, E, is a function of the Förster parameter, $R_o$, and of the distance between the donor and the acceptor, R:

$$E=[1+(R/R_o)^6]^{-1}$$

wherein the Förster parameter (in angstroms, Å), is:

$$R_0 \text{ (in Å)} = (0.211 \times 10^{-5})(n^{-4} Q_{DK}^2 J)^{1/6}$$

wherein n is the refractive index of the medium, $Q_D$ is the donor quantum yield in the absence of the acceptor, $\kappa^2$ is the orientation factor relating the donor acceptor transition dipoles, and J is the spectral overlap integral of the donor emission spectrum and the acceptor excitation spectrum.

If one performs FRET experiments under conditions where $R_o$ is constant, measured changes in E permit detection of changes in R, and, if one performs experiments under conditions where $R_o$ is constant and known, the measured absolute magnitude of E permits determination of the absolute magnitude of R.

With fluorochromes and chromophores known in the art, FRET is useful over distances of about 1 nm to about 15 nm, which are comparable to the dimensions of biological macromolecules and macromolecule complexes. Thus, FRET is a useful technique for investigating a variety of biological phenomena that produce changes in molecular proximity. When FRET is used as a detection mechanism, colocalization of proteins and other molecules can be imaged with spatial resolution beyond the limits of conventional optical microscopy.

A FRET assay to detect and quantify binding between two molecules, molecule 1 and molecule 2, may be configured as follows: a reaction mixture is prepared by combining molecule 1 labeled with a molecule according to Formula (I) where detectable group X is a fluorescent moiety and molecule 2 is labeled with a fluorescent moiety Y or a chrompohore Y, wherein X and Y are able to participate in FRET. Complex formation results in increased proximity between X and Y, and, correspondingly, in increased FRET. The progress of the reaction is monitored by observing the increase in FRET. Equilibrium association and dissociation constants may be extracted from the concentration-dependence of the reaction.

A FRET assay to detect and quantify proteolytic activity may be configured as follows: a reaction mixture is prepared by combining a) a substrate molecule labeled at site 1 with Formula (I) wherein detectable group X is a fluorescent moiety and labeled at site 2 with fluorochrome Y, wherein sites 1 and 2 are on opposite sides of the proteolytic-cleavage site, and wherein X and Y are able to participate in FRET, and b) a sample containing a proteolytic enzyme. Cleavage of the substrate molecule by the proteolytic enzyme results in decreased proximity between X and Y and, correspondingly, in decreased FRET. The progress of the reaction is monitored by observing the decrease in FRET.

A FRET assay to detect conformation change within molecule 1 induced upon interaction with molecule 2, may be configured as follows: a reaction mixture is prepared by combining (a) molecule 1 labeled at one site with fluorochrome X according to the current invention and labeled at another site with fluorochrome Y, wherein X and Y are able to participate in FRET, and (b) molecule 2. Conformation change within molecule 1 induced upon interaction with molecule 2 results in a change in proximity between X and Y, and, correspondingly, a change in FRET. The progress of the reaction is monitored by observing the change in FRET.

A FRET assay to measure the distance between two sites, 1 and 2, within a molecule of interest, may be configured as follows: the molecule of interest is labeled at site 1 with fluorochrome X according to the current invention and is labeled at site 2 with fluorochrome Y, wherein X and Y are able to participate in FRET; fluorescence excitation and emission spectra are collected for X and Y; and the distance, R, is calculated as described supra.

Fluorescence emission intensity, lifetime, polarization, aniosotropy and FRET are further described in the following references: Brand, L. and Johnson, M. L., Eds., *Fluorescence Spectroscopy* (Methods in Enzymology, Volume 278), Academic Press (1997), Cantor, C. R. and Schimmel, P. R., *Biophysical Chemistry Part 2*, W. H. Freeman (1980) pp. 433-465. Dewey, T. G., Ed., *Biophysical and Biochemical Aspects of Fluorescence Spectroscopy*, Plenum Publishing (1991). Guilbault, G. G., Ed., *Practical Fluorescence*, Second Edition, Marcel Dekker (1990). Lakowicz, J. R., Ed., *Topics in Fluorescence Spectroscopy: Techniques* (Volume 1, 1991); *Principles* (Volume 2, 1991); *Biochemical Appli-* cations (Volume 3, 1992); *Probe Design and Chemical Sensing* (Volume 4, 1994); *Nonlinear and Two-Photon Induced Fluorescence* (Volume 5, 1997); *Protein Fluorescence* (Volume 6, 2000), Plenum Publishing.

Fluorescence imaging using epi-illumination, confocal, or total-internal-reflection optical microscopy permits characterization of the quantities, locations, and interactions of fluorochrome-labeled target materials within cells. All fluorescence observables that can be analyzed in vitro—emission intensity, emission lifetime, fluorescence correlation, FP/FA, and FRET—also can be analyzed in cells (See Nakanishi et al. *Anal. Chem.* 73:2920-2928 (2001); Maiti, S. et al. *Proc. Natl. Acad. Sci. USA* 94: 11753-11757 (1997); Eigen and Rigler, *Proc. Natl. Acad. Sci. USA* 91:5740-5747 (1994) for example of uses of fluorescence in cells).

The bis-transition-metal-chelate molecules of this invention may be used to label target-sequence-containing molecules within cells. The bis-transition-metal-chelate molecules of this invention may be introduced into cells by diffusion (for bis-transition-metal-chelate molecules capable of traversing biological membranes) or by microinjection, electroporation, or vesicle fusion (for any bis-transition-metal-chelate molecule). The target-sequence-containing molecules may be introduced into cells by microinjection, electroporation, or vesicle fusion, or by expression of recombinant genes in situ.

In one embodiment, a target-sequence-containing protein produced by expression of a recombinant gene within cells is contacted with a bis-transition-metal-chelate molecule of this invention by incubating cells in medium containing the bis-transition-metal-chelate molecule. Following labeling, and optionally following further manipulations, the cells are imaged using an epi-illumination, confocal, or total-internal-reflection optical microscope with an optical detector, such as a CCD camera, an intensified CCD camera, a photodiode, or a photomultiplier tube, and fluorescence signals are analyzed.

The fluorescent molecules of the present invention also can be used, in vitro or in vivo, in single-molecule fluorescence assays with single-molecule detection, wherein fluorescence emission intensity, fluorescence correlation, FP/FA, or FRET is analyzed from individual single molecules.

The fluorescent molecules of the present invention also can be used, in vitro or in vivo, in fluorescence assays with "multiplex" detection, wherein a plurality of different fluorescent molecules are attached to a plurality of different primary molecules, molecule 1a, 1b, . . . 1n, with each primary molecule being specific for a different secondary component, 2a, 2b, . . . 2n, in order to monitor a plurality of reactions between primary molecules and secondary molecules in a single reaction mixture. According to this method of use, each of the primary molecules is separately labeled with a fluorochrome having a different, distinguishable excitation and/or emission wavelength. The primary molecules are then reacted, as a group, with the secondary molecules, as a group, and fluorescence is monitored at each of different, distinguishable excitation and/or emission wavelengths.

The fact that the present invention is compatible with fluorochromes having different, distinguishable excitation and emission wavelengths (see, e.g., Table 1 for excitation maxima and emission maxima of derivatives of Cy3, Cy5, and Cy7 in Examples), makes the invention particularly important for applications involving multiplex detection. Most or all of the assays above, in vitro or in vivo, can be adapted for high-throughput screening, using formats, equipment, and procedures apparent to persons skilled in the art.

Examples of fluorochromes and chromophores suitable for use in assays above, in conjunction with the molecules of the invention, are presented in Haugland R. P. *Handbook of Fluorescent Probes and Research Chemicals*, Molecular Probes, sixth edition (1996), ISBN 0-9652240-0-7 (Spence, MTZ, Ed). Said fluorochromes and chromophores can be incorporated into polypeptides and other molecules of interest by any suitable method, many of which are well known in the art, including, but not limited to, chemical synthesis, enzymatic synthesis, ribosomal synthesis, chemical ligation, chemical modification, and hapten binding (see Haugland R. P. *Handbook of Fluorescent Probes and Research Chemicals*, supra). Alternatively, fusions of autofluorescent proteins, such as green fluorescent protein, to a polypeptide of interest can be encoded as nucleic-acid fusion constructs, produced in cells, and analyzed in cells or in vitro.

The methods of the invention may be used in many areas of biology and biological research including drug screening, diagnostics and academic research.

It further is contemplated that the bis-transition-metal-chelate molecules of the invention may be used for immobilization and/or affinity-purification of target-sequence-containing molecules.

Immobilization may be accomplished by: (a) covalently attaching a bis-transition-metal-chelate molecule to a surface or other solid support (via detectable group X or via a linker); (b) contacting the resulting bis-transition-metal-chelate-molecule-containing surface or other solid support with a solution containing a target-sequence-containing target material; and (c) optionally washing the surface or the solid support to remove unbound material.

Affinity purification may be accomplished by: (a) covalently attaching a bis-transition-metal-chelate molecule to a surface or other solid support, (b) contacting the resulting bis-transition-metal-chelate-molecule-containing surface or other solid support with a solution containing a target-sequence-containing molecule, (c) optionally washing the surface or other solid support to remove unbound material, and (d) eluting the target-sequence-containing molecule with a low-molecular-weight monothiol (e.g., β-mercaptoethanol) or, preferably, a low-molecular-weight dithiol (e.g., dithiothreitol or ethanedithiol).

Kits According to the Invention

In some embodiments, the molecules of the invention are prepared as solutions to be used in kits and methods such as electrophoresis. Preferably, such solutions are provided "ready-to-go," i.e., they can be used directly to stain gels without further dilution.

In one embodiment, the molecules according to Formula (I) are provided in the form of a concentrated stock solution. The stock solution may be provided in any convenient or suitable degree of concentration. For example, a stock solution may be concentrated from about 500 fold (500×), about 200×, about 100×, about 50×, about 25×, about 10×, or about 2× more concentrated that the staining solution. That is, in order to produce a staining solution from a 500× stock solution, the stock solution would be diluted 500-fold. A suitable concentration may be up to about a 50 molar (M) concentration, preferably a 10M concentration, more preferably a 1M concentration. The molecules of the invention will be provided in solution, such as in an aqueous solution. Preferably, the stock solution will include a suitable preservative, the selection of which will be readily apparent to those having skill in the art. A preferred preservative is sodium azide.

In an alternative embodiment, the molecules of the invention will be provided in a ready-to-use form, such as a gel staining solution. The gel staining solution is provided in a suitable concentration for immediate use in the gel electrophoresis of interest (i.e., in a concentration of 1×). Suitable concentrations for a gel staining solution are from about 0.1 µM to about 100 µM, preferably from about 1 µM to about 10 µM.

In this embodiment, the molecules of the invention will be provided in a solution compatible with the particular gel electrophoresis of interest. Preferably, the gel staining solution will be supplied in solution with a buffer compatible with the particular gel electrophoresis application, more preferably the gel staining solution will be provided in a solution having the same buffer as the loading buffer used in the gel.

A representative "ready-to-use" gel staining solution includes a 500 mL amber bottle containing: 500 mL of a solution of 0.2 µM of molecules according to the invention in 20 mM phosphate at a pH of 7.8 and 2 mM sodium azide as a preservative.

Generally, liquid and other components of the kits are provided in containers, which are typically resealable. The containers may be transparent, translucent or opaque. Preferably, the container for stock solutions and gel stain solutions is an amber bottle. A preferred container is an Eppendorf tube, particularly a 1.5 ml Eppendorf tube. A variety of caps may be used with the liquid container. Generally preferred are tubes with screw caps having an ethylene propylene O-ring for a positive leak-proof seal. A preferred cap uniformly compresses the O-ring on the beveled seat of the tube edge. Preferably, the containers and caps may be autoclaved and used over a wide range of temperatures (e.g., +120° C. to −200° C.) including use with liquid nitrogen. Other containers can be used.

The invention also provides a kit including one or more molecules according to Formula (I) and at least one target material including at least one target sequence of the form: $(H)_i$, wherein H is histidine and i is an integer of from 4 to 12 (i.e., SEQ ID NOS. 1-9, respectively), preferably 4 to 8, and most preferably 6.

A kit according to the invention may also generally includes at least one molecule according to Formula (I) and at least one reagent the promotes the formation of a complex between the molecule of Formula (I) and a target sequence of the invention.

In a further aspect, the invention relates to kits comprising one or more molecules of the invention. Optionally, such kits further comprise one or more of the following: (a) one or more gels; (b) one or more containers including one or more molecules including a target sequence, the target sequence including an amino acid sequence of the form $(H)_i$, wherein H is histidine and i is an integer of from 4 to 12; (c) one or more containers including one or more antibodies having an epitope having an amino acid sequence of the form $(H)_i$, wherein H is histidine and i is an integer of from 4 to 12; (d) one or more containers including one or more protein-denaturing solutions; (g) one or more containers including one or more sample loading buffers; and (h) one or more sets of instructions. Optionally, the molecule of the invention is provided on one or more solid supports. The solid supports are preferably a purification column, a cellulose blot or a bead. Optionally, one or more of the additional liquid elements of the kit are provided in an appropriate container such as a sealed vial or the like.

Antibodies used in the kits will have an epitope include an amino acid sequence of the form $(H)_i$, wherein H is histidine and i is an integer of from 4 to 12 include. Examples of suitable epitopes, by way of non-limiting example, include polyclonal antibodies, such as those available from Medical and Biological Laboratories, Inc. (Nagoya, Japan); monoclonal antibodies (mAbs) such as 4D11 (Abcam, Inc.; Cambridge, Mass.), 27E8 (Cell Signaling Technology, Inc.; Beverly, Mass.), IPA2C6.1 (Exalpha Biologicals, Inc.; Watertown, Mass.), and those described in published PCT application WO 96/26963 (EMD Biosciences, Inc., Novagen Brand, Madison, Wis.); other mAbs available from, e.g., Oncogene Research Products (San Diego, Calif.), BD Biosciences Clontech (Palo Alto, Calif.), and others; and single-chain antibodies, such as that derived from the anti-His tag antibody 3D5 (Kaufmann et al., *J Mol Biol*. 318: 135-147, 2002).

One type of kit of the invention comprises a solution comprising one or more molecules according to Formula (I), wherein the one or more molecules are present in a concentration sufficient to stain molecules including a target sequence, the target sequence comprising an amino acid sequence of the form $(H)_i$, wherein H is histidine and i is an integer of from 4 to 12, and wherein said target molecules are in an electrophoretic medium.

A typical method for staining using electrophoretic media in a gel format that can be carried out at ambient temperature includes the steps of: fixing the gel (e.g., incubating the gel in an aqueous solution having 40% ethanol and 10% acetic acid for about 1 hour); rinsing the fixed gel one or more times with distilled water for about 10 minutes; incubating the gel in a staining solution for about 1 hour; and washing the gel one or more times with 20 mM sodium phosphate, pH 7.8. For visualization, the gel is placed, for example, on a transilluminator operating at a wavelength of 302 nm uv.

Typically, the fixing solution contains a polar organic solvent, for example, an alcohol. Preferably, the polar organic solvent is an alcohol having 1-6 carbon atoms, or a diol or triol having 2-6 carbon atoms. Preferred alcohols are methanol or ethanol mixed with acetic acid. The alcohols, in one illustrative example, are present in an aqueous solution of about 50% ethanol or methanol with 10% acetic acid. The gel can be fixed in multiple sequential steps. Essentially, the gel is immersed in the fixing solution for example, for at least 20 minutes and then removed from the solution and new solution added for at least 3 hours and up to 24 hours.

The staining solution can be prepared in a variety of ways, which is dependent on the medium the sample is in. A particularly preferred staining solution is one that is formulated for detection of affinity tags in a gel. Specifically, the staining solution comprises a fluorescent compound of the present invention in an aqueous solution; optionally the staining solution comprises an organic solvent and a buffering component. The selection of the fluorescent compound dictates, in part, the other components of the staining solution. Any of the components of the staining solution can be added together or separately and in no particular order wherein the resulting staining solution is added to the gel. Alternatively, the components of the staining solution can be added to a gel in a step-wise fashion. The fluorescent compound is prepared by dissolving it in a solvent, such as water, DMSO, DMF or methanol. Usually the fluorescent compound is at a final concentration of about 0.01 µM to 100 mM, for example, 0.05 µM to 10 µM, in certain illustrative examples, from 0.05 µM to 1 µM. In another example, the compound is present at a final concentration of 0.1 µM to 0.3 µM, more specifically 0.2 µM.

In certain illustrative embodiments, the pH of the staining solution is 7-10, more specifically, for example, the pH is 7.1 to 10.0, 7.4 to 8.8, 7.6 to 8.2, 7.7 to 7.9, or 7.8. The pH of the staining mixture is optionally modified by the inclusion of a buffering agent in addition to or in place of an alkaline component. Any buffering agent that maintains an alkaline environment and is compatible with the affinity tag and fusion protein in the sample is suitable for inclusion in the staining mixture. For example, buffers used in the staining mixture can be Tricine, BES, phosphate or Tris. In certain illustrative embodiments, the buffer is phosphate or Tris. In addition, the staining solution can include an effective amount of a preservative. Many preservatives are known in the art and can be used with the present invention. For example, sodium azide can be included in the staining solution.

Optionally, the staining solution contains a metal ion salt. Nickel ions and cobalt ions have affinity for both the bis-transition metal chelate probes of the present invention and the poly-histidine affinity tag, therefore nickel or cobalt salts are optionally included in staining solutions of the present invention. An exemplified salt is nickel chloride but any nickel or cobalt salt known to one skilled in the art can be used. The salt is typically present in the staining solution at a concentration of about 10 nm to 1 mM; preferably the concentration is about 1 µM to 200 µM.

After staining and before detection (i.e. visualization), the gel can be rinsed in a rinse solution that is similar in composition, or identical in composition, to the staining solution except that it does not include the bis-transition-metal-chelate compound of the present invention.

EXAMPLE 1

Synthesis of $(Ni^{2+}-NTA)_2$-Cy3

A. Synthesis of $(NTA)_2$-Cy3

N-(5-amino-1-carboxypentyl)iminodiacetic acid (Dojindo; 26 mg, 80 µmol) was dissolved in 1.6 ml 0.1M sodium carbonate and was added to Cy3 bis-succinimidyl-ester ("Cy3 Reactive Dye" from Amersham-Pharmacia Biotech). Following reaction for 1 hour (with vortexing at 15-min intervals) at 25° C. in the dark, products were purified from excess N-(5-amino-1-carboxypentyl)iminodiacetic acid using a Sep-Pak C18 cartridge ((Millipore; pre-washed with 10 ml of acetonitrile and 10 ml water; washed with 20 ml water; eluted with 1 ml 60% methanol), dried, re-dissolved in 200 µl methanol, and purified by preparative TLC [1000 Å silica gel (Analtech); NH$_4$OH: ethanol:water 55:35:10 v/v/v]. Three bands were resolved, corresponding to $(NTA)_2$-Cy3 ($r_f$=0.2), $(NTA)_1$-Cy3 mono acid ($r_f$=0.5), and $(NTA)_2$-Cy3 bis acid ($r_f$=0.8). $(NTA)_2$-Cy3 was eluted using 60% methanol, dried, re-dissolved in 2 ml water and quantified spectrophotometrically ($\epsilon_{550}$-150,000M$^{-1}$ cm$^{-1}$). The yield was 64 nmol, 8%. ES-MS: m/e 1197.0 (calculated 1197.4).

B. Synthesis of $(Ni^{2+}-NTA)_2$-Cy3

NiCl$_2$ (Aldrich; 350 µmol of NiCl$_2$ in 3 µl of 0.01N HCl) was added to $(NTA)_2$-Cy3 (70 nmol in 2 ml water), and the solution was brought to pH 7 by addition of 0.8 ml 50 mM sodium acetate (pH 7), 200 mM NaCl. Following reaction for 30 min. at 25° C. in the dark, the product was purified using a Sep-Pak C18 cartridge ((Millipore; procedure as above) and dried. ES-MS: m/e 1316.8 (calculated 1315.7). Ni$^{2+}$ content [determined by performing analogous reaction with $^{63}$NiCl$_2$ (New England Nuclear) and quantifying reactivity in product by scintillation counting in Scintiverse II (Fischer)]: 1.4 mol Ni$^{2+}$ per mol. Spectroscopic properties are reported in Table 1.

TABLE 1

(XXV)

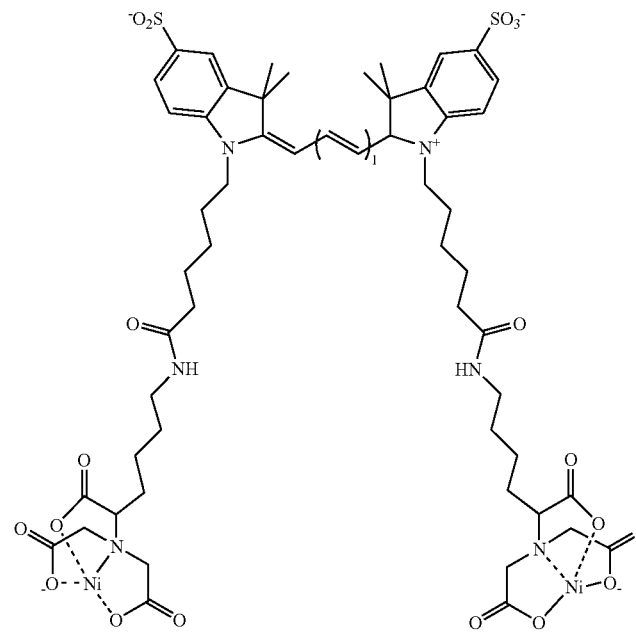

Spectroscopic Properties of $(Ni^{2+}-NTA)_2$-Cy3 and Ni$^{2+}-NTA)_2$-Cy3[a]

| fluorochrome | $\lambda_{max, exc}$(nm) | $\lambda_{max, em}$(nm) | quantum yield (Q) |
|---|---|---|---|
| $(Ni^{2+}-NTA)_2$-Cy3 | 552 | 565 | 0.04 |
| $(Ni^{2+}-NTA)_2$-Cy5 | 650 | 668 | 0.05 |

[a]Ni$^{2+}$-free analogues exhibit identical $\lambda_{max, exc}$ and $\lambda_{max, em}$ and 3.8-fold higher Q (with the higher Q presumably reflecting the unavailability of nonradiative decay involving Ni$^{2+}$ unoccupied d orbitals).

EXAMPLE 2

Synthesis of ($Ni^{2+}$-NTA)$_2$-Cy5

A. Synthesis of (NTA)$_2$-Cy5

N-(5-amino-1-carboxypentyl)iminodiacetic acid (Dojindo; 40 mg; 125 μmol) was dissolved in 0.8 ml 0.1M sodium carbonate and was added to Cy5 bis-succinimidyl-ester ("Cy5 Reactive Dye" Amersham-Pharmacia Biotech; 800 nmol). Following reaction for 1 h (virtexed at 15 minute intervals) at 25° C. in the dark, products were purified from excess N-(5-amino-1-carboxypentyl)iminodiacetic acid using a Sep-Pak C18 cartridge (Millipore; procedure as above), dried, re-dissolved in 200 μl methanol, and purified in 100 μm portions by preparative TLC [silica gel, 1000 Å (Analtech); NH$_4$OH:ethanol:water in a 55:35:10 v/v/v. Three bands were resolved, corresponding to (NTA)$_2$-Cy5 ($r_f$=0.2), (NTA)$_1$-Cy5 mono acid ($r_f$=0.6), and (NTA)$_2$-Cy5 bis acid ($r_f$=0.8). The (NTA)$_2$-Cy5 was eluted with 60% methanol, dried, re-dissolved in 2 ml water and quantified spectrophotometrically ($\epsilon_{550}$=250,000$M^{-1}$ $cm^{-1}$). Yield: 60 nmol; 7.5%.

B. Synthesis of ($Ni^{2+}$-NTA)$_2$-Cy5

NiCl$_2$ (Aldrich; 90 nmol in 1 μl of 0.01 N HCl) was added to (NTA)$_2$-Cy5 (30 mmol in 1 ml water), and the solution was bought to pH 7 by addition of 0.5 ml 50 mM sodium acetate (pH 7), 70 mM NaCl. Following reaction for 30 min. at 25° C. in the dark, the product was purified using a Sep-Pak C18 cartridge (Millipore; procedure as above) and dried. ES-MS: mle 1341.0 (calculated 1341.7). Spectroscopic properties are reported in Table 1.

EXAMPLE 3

Preparation of a C-Terminally Hexahistidine Tagged Derivative of the Transcriptional Activator CAP (CAP-His$_6$)

A. Preparation of CAPHis$_6$

Plasmid pAKCRP-His$_6$ encodes CAP-His$_6$ under the control of bacteriophage T7 gene 10 promotor. Plasmid AKCRP-His$_6$ was constructed from plasmid pAKCRP (as described in Kapanidis, A. et al., *J. Mol. Biol.* 312:453-468 (2001) by using site-directed mutagenesis (as described in Kukel, et al., *J. Meths. Enzymol.*, 204:125-138 (1991)) to insert six His codons (CAC-CAC-CAC-CAC-CAC-CAC) after codon 209 of the crp gene.

To prepare CAP-His$_6$, a culture of *E. coli* strain BL21 (DE3) (Novagen) transformed with pAKCRP-His$_6$ was shaken at 37° C. in 1 L LB (as described in Miller, J., *Experiments in Molecular Genetics*, Cold Spring Harbor Laboratory, Cold Spring Harbor, N.Y. (1972)) containing 200 mg/ml ampicillin until $OD_{600}$=0.5, induced by addition of isopropyl-thio-β-D-galactoside to 1 mM, and shaken an additional 3 h at 37° C. The culture was harvested by centrifugation (4,500×g; 15 min. at 4° C.), the cell pellet was re-suspended in 15 ml buffer A [20 mM Tris-HCl (pH 7.9), 500 mM NaCl, 5 mM imidazole], cells were lysed by sonication, and the lysate was cleared by centrifugation (30,000×g; 30 min. at 4° C.). The sample was adjusted to 15 ml with buffer A, adsorbed onto 2 ml $Ni^{2+}$-NTA agarose (Qiagen) in buffer A, washed with 12 ml buffer A containing 20 mM imidazole, and eluted with 6×1 ml buffer A containing 200 mM imidazole.

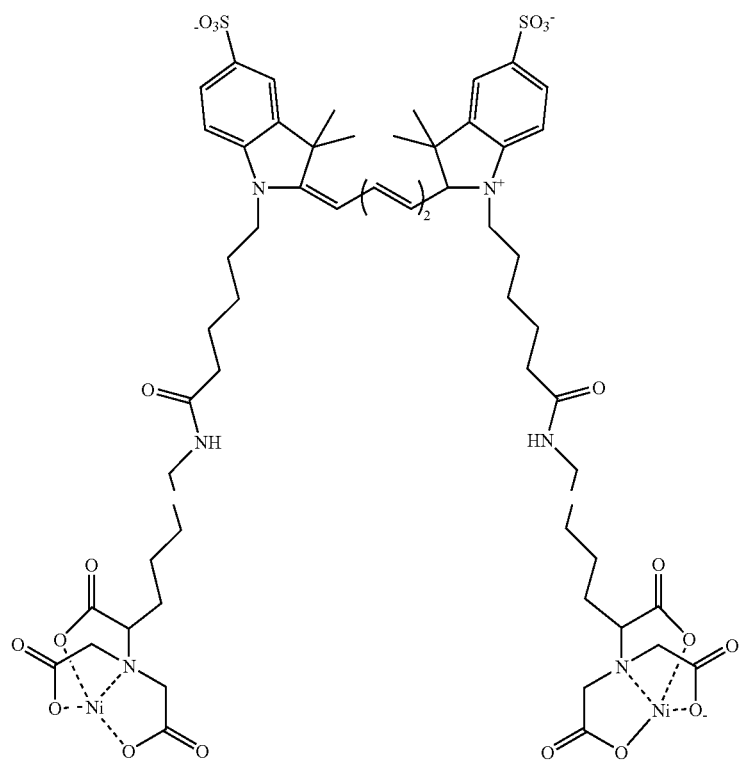

(XXVI)

Fractions containing CAP-His$_6$ were pooled, desalted twice into buffer B [40 mM Tris-HCl (pH 8), 100 mM NaCl, 1 mM dithiothreitol, 5% glycerol] by gel-filtration chromatography on NAP-10 (Amersham-Pharmacia Biotech), quantified spectrophotometrically ($\epsilon_{278,\,protomer}$=20,000 M$^{-1}$ cm$^{-1}$), and stored in aliquots at −80° C. Yield ~20 mg/L culture. Purity >99%.

EXAMPLE 4

Verification of Affinity and Specificity of Association of (Ni$^{2+}$-NTA)$_2$Cy3 and (Ni$^{2+}$-NTA)$_2$Cy5 with Target Material Affinity and specificity of association of the probe with target material were evaluated using fluorescence anisotropy assays (methods as in Jameson and Dwyer, *Methods Enzymol.*, 246:283-300 (1995)). Formation of a complex of the probe with a His$_6$-tagged protein was detected as an increase in fluorescence anisotropy, A, arising from the increase in molecular size and corresponding decrease in rotational dynamics.

Reaction mixtures [200 μl, in 100 μl quartz micro-cuvettes (Starna)] contained 50 nM of (Ni$^{2+}$-NTA)$_2$-Cy3 or (Ni$^{2+}$-NTA)$_2$-Cy5 in buffer C [40 mM Tris-HCl (pH 8), 100 mM NaCl, 1 mM dithiothreitol, 0.5 mM imidazole, 0.2 mM cAMP, 100 μg/ml bovine serum albumin, and 5% glycerol]. Reaction mixtures were titrated with 0-3 μM CAP-His$_6$ (or CAP) by successive addition of 0.5-4 μl aliquots of 2-4 μM CAP-His$_6$ (or CAP) in the same buffer. Fluorescence anisotropy was determined at the start of the titration and 5 min after each successive addition in the titration. All solutions were maintained at 25° C.

Fluorescence measurements were performed using a commercial steady-state fluorescence instrument (QM-1, PTI) equipped with T-format Glan-Thompson polarizers (PTI). Excitation wavelengths were 530 nm for (Ni$^{2+}$-NTA)$_2$-Cy3 and 630 nm for (Ni$^{2+}$-NTA)$_2$-Cy5; emission wavelengths were 570 nm for (Ni$^{2+}$-NTA)$_2$-Cy3 and 670 nm for (Ni$^{2+}$-NTA)$_2$-Cy5. Slit widths were 10 nm. Fluorescence emission intensities were corrected for background by subtraction of fluorescence emissions intensities for control reactions containing identical concentrations of CAP-His$_6$ or CAP but not containing probe.

Fluorescence anisotropy, A, was calculated using: A=(I$_{VV}$−GI$_{VH}$)/(IVV+2G$_{VH}$) where I$_{VV}$ and I$_{VH}$ are the fluorescent intensities with the excitation polarizer at a vertical position and the emission polarizers at vertical and horizontal positions, respectively, and G is the grating correction factor. Data were plotted as: (A−A$_0$/A$_0$) where A is the fluorescence anisotropy in the presence of the indicated concentration of CAP-His$_6$ or CAP, and A$_0$ is the fluorescence anisotropy in the absence of CAP-His$_6$ or CAP. Equilibrium dissociation constants were calculated using linear regression.

Figure 2:
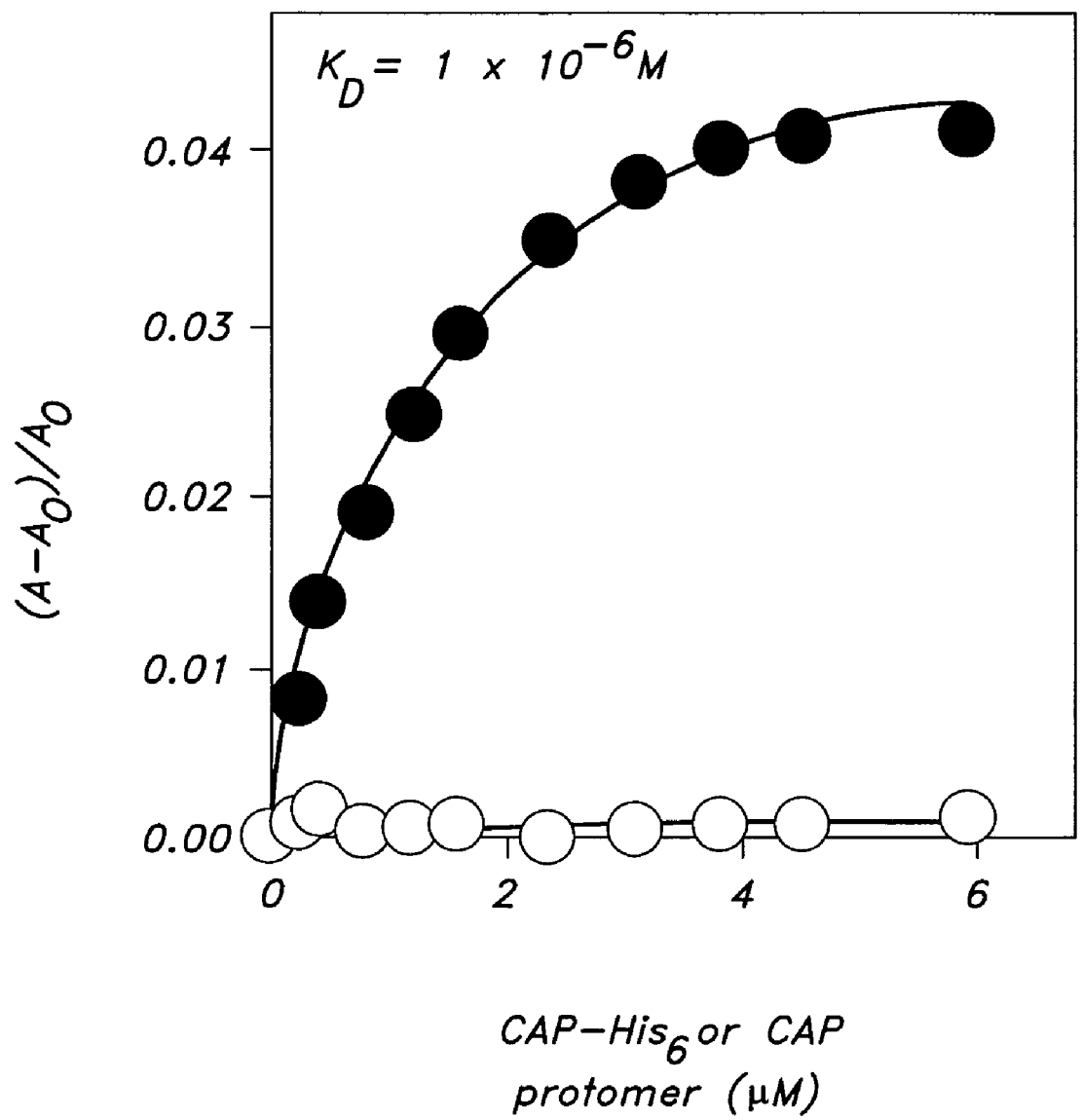
FIGS. 2 and 3 show results of fluorescence anisotropy experiments verifying specific interactions between bis-transition-metal-chelate probes according to the invention with a hexahistidine-tagged protein.

Referring now to FIG. 2, a graphical representation of results of titration of (Ni$^{2+}$-NTA)$_2$-Cy3 with His$_6$-CAP is shown (filled circles). Specific interaction between (Ni$^{2+}$-NTA)$_2$-Cy3 and CAP-His$_6$ is evidenced by a large, saturable increase in fluorescence anisotropy. High affinity of interaction is evidenced by a low equilibrium dissociation constant (K$_D$=1.0 μM). Specificity of interaction is evidenced by the absence of a significant increase in fluorescence anisotropy in a control titration with CAP (open circles; >95% specificity).

Figure 3:
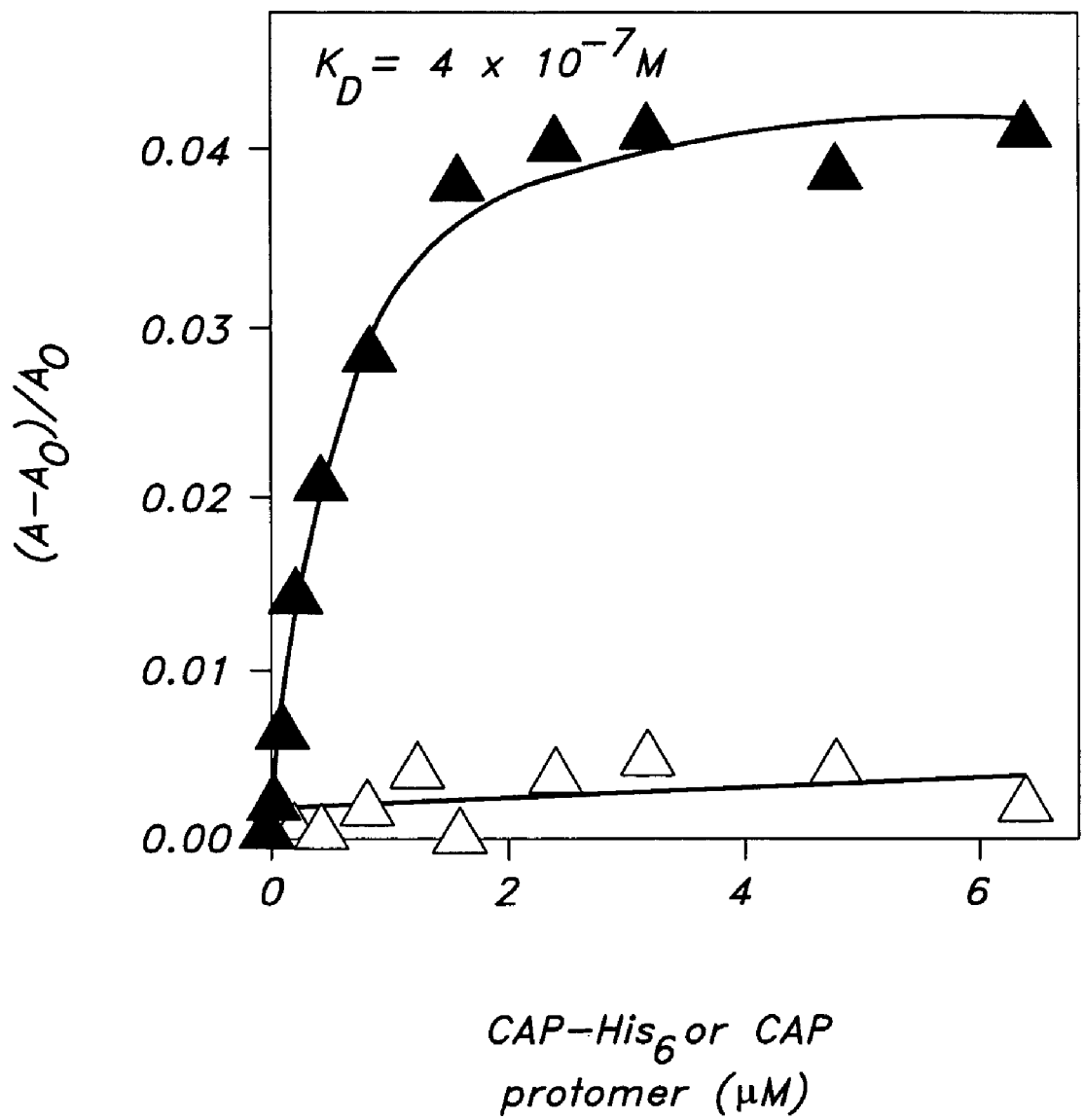

Referring now to FIG. 3, a graphical representation is shown of titration of (NTA)$_2$-Cy5 with CAP-His$_6$ is shown (filled circles). Specific interaction between (Ni$^{2+}$-NTA)$_2$-Cy5 and His$_6$-CAP is evidenced by a large, saturable increase in fluorescence anisotropy. High affinity of interaction is evidenced by a low equilibrium dissociation constant (K$_D$=0.4 μM). Specificity of interaction is evidenced by the absence of a significant increase in fluorescence anisotropy in a control titration with CAP (open circles; >95% specificity).

EXAMPLE 5

Verification of Affinity, Specificity, and Stoichiometry of Association of (Ni$^{2+}$-NTA)$_2$-Cy3 and (Ni$^{2+}$-NTA)$_2$-Cy5 with Target Material: FRET The affinity, specificity, and stoichiometry of interactions between probes according to the invention and His$_6$ also were verified using FRET assays. A His$_6$-tagged protein-DNA complex, (CAP-His$_6$)-DNA$^F$, was prepared. FRET assays using the probes according to the invention then were performed to verify interactions, to detect a target material, and to measure an intermolecular distance.

A. Preparation of DNA$^F$

DNA$^F$, 53 base pair fluorescein-labelled DNA fragment containing the consensus DNA site for CAP (fluorescein incorporated at position -9 relative to the consensus DNA site for CAP) was prepared as described in Ebright, R. et al., *J. Mol. Biol.* 312:453-468 (2001).

B. FRET Assays-Standard Titrations

Reaction mixtures (200 μl, in 50 μl quartz micro-cuvettes (Starna)) contained 5 nM DNA$^F$ and 50 nM CAP-His$_6$ (or CAP) in buffer C. Reaction mixtures were titrated with 0-3.2 μM of (Ni$^{2+}$-NTA)$_2$-Cy3 or (Ni$^{2+}$-NTA)$_2$-Cy5 by successive addition of 0.3-1.2 μl aliquots of 30-300 μM of (Ni$^{2+}$-NTA)2-Cy3 or (Ni$^{2+}$-NTA)$_2$-Cy5 in the same buffer. Fluorescence emission was determined at the start of the titration and 5 min after each successive addition in the titration. All solutions were maintained at 25° C.

Fluorescence emission intensities, F, were measured using a commercial steady-state fluorescence instrument (QM-1, PTI) equipped with T-format Glan-Thompson polarizers (PTI) set at 54.7° ("magic angle"). Excitation wavelength was 480 nm; emission wavelength range was 500-600 nm (titrations with (Ni$^{2+}$-NTA)$_2$-Cy3) or 500-700 nm (titrations with (Ni$^{2+}$-NTA)$_2$-Cy5; excitation slit width was 10 nm; emission slit width was 15 nm. Fluorescence emission intensities were corrected for background (by subtraction of fluorescence emission intensities for control reaction mixtures containing identical concentrations of (Ni$^{2+}$-NTA)$_2$-Cy3 or (Ni$^{2+}$-NTA)$_2$-Cy5, but not containing CAP-His$_6$ or CAP) and for dilution.

Efficiencies of FRET, E, were calculated as: E=1−(F$^{520,480}$/F$^{520,480}$$_o$) where F$^{520,480}$ is the fluorescence emission intensity of the fluorescein label at the indicated concentration of (Ni$^{2+}$-NTA)$_2$-Cy3 or (Ni$^{2+}$-NTA)$_2$-Cy5 and F$_{520/480_o}$ is the fluorescence emission intensity of the fluorescein label at 0 μM of (Ni$^{2+}$-NTA)$_2$-Cy3 or (Ni$^{2+}$-NTA)$_2$-Cy5. Data were plotted as E vs. titrant concentration, and binding curves and equilibrium dissociation constants were calculated using non-linear regression (as described in Gunasekera, A. et al., *J. Biol. Chem.*, 267:14,713-14,720 (1992)).

Figure 5:
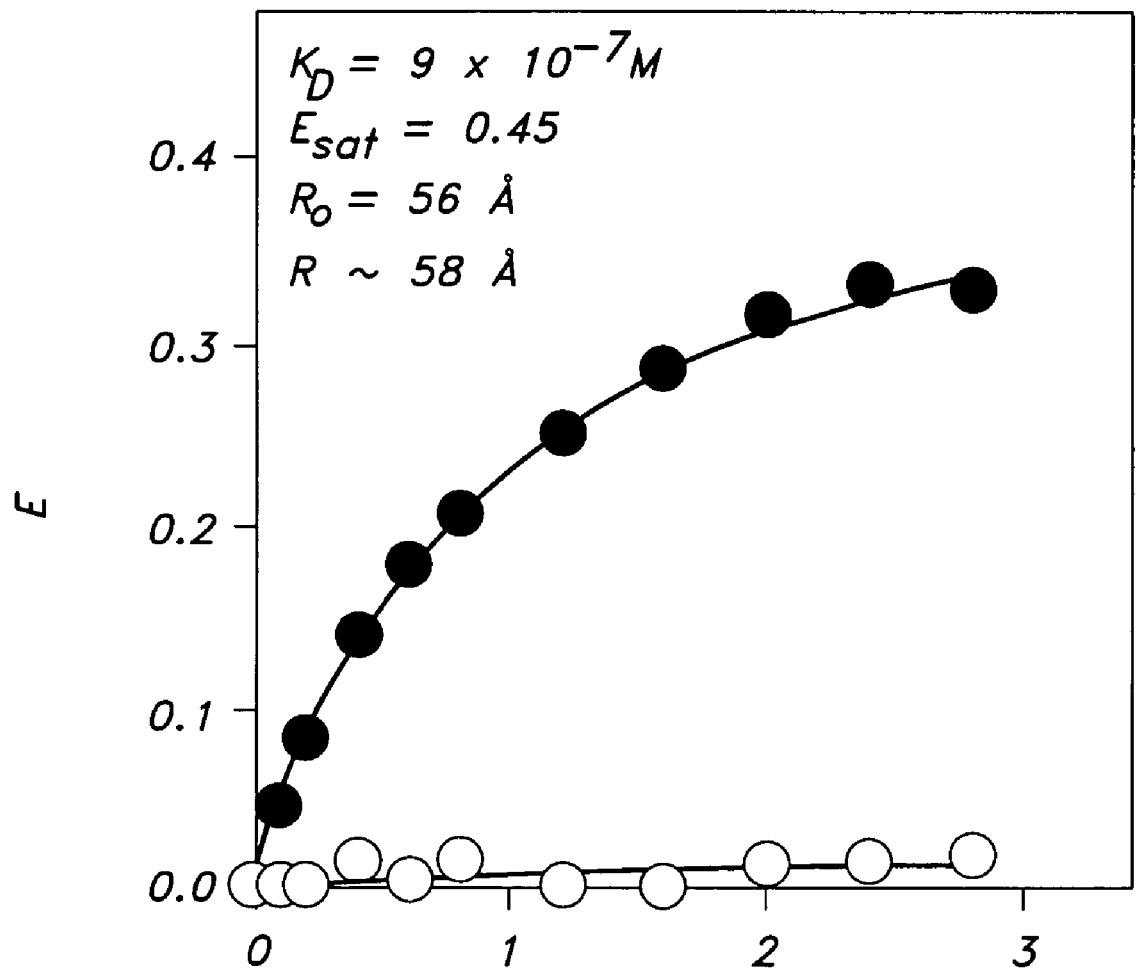
FIGS. 5 and 6 show results of FRET experiments verifying high-affinity, specific interactions of bis-transition-metal-chelate probes according to the present invention with a hexahistidine tagged protein.

Referring now to FIG. 5, a graphical representation of results of titration of the (CAP-His$_6$)-DNA$^F$ complex with (Ni$^{2+}$-NTA)$_2$-Cy3 is shown (filled circles). Specific interaction between the (CAP-His$_6$)-DNA$^F$ complex and (Ni$^{2+}$-NTA)$_2$-Cy3 is evidenced by a large, saturable increase in FRET. High affinity of interaction is evidenced by a low equilibrium dissociation constant (K$_D$=0.9 μM). Specificity of interaction is evidenced by the absence of a significant increase in FRET in a control titration with the CAP-DNA$^F$ complex (open circles; >95% specificity).

Figure 6:
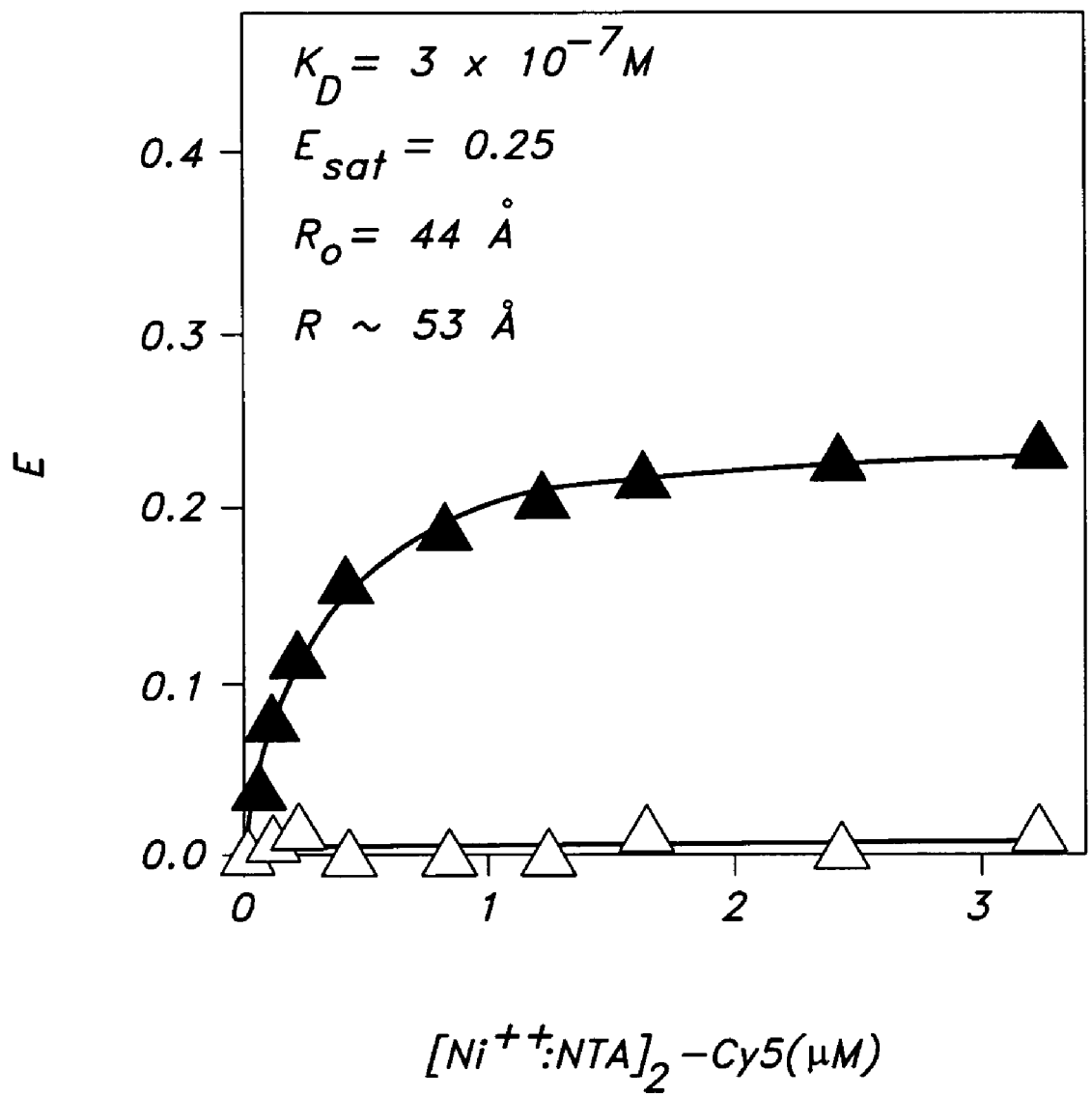

Referring now to FIG. 6, a graphical representation of results of titration of the (CAP-His$_6$)-DNA$^F$ complex with ($Ni^{2+}$-$NTA$)$_2$-Cy5 is shown (filled triangles). Specific interaction between the (CAP-$His_6$)-$DNA^F$ complex and ($Ni^{2+}$-$NTA$)$_2$-Cy5 is evidenced by a large, saturable increase in FRET. High affinity of interaction is evidenced by a low equilibrium dissociation constant ($K_D$=0.3 μM). Specificity of interaction is evidenced by the absence of a significant increase in FRET in a control titration with the CAP-$DNA^F$ complex (open triangles; >95% specificity).

C. FRET Assays-Stoichiometric Titrations

Stoichiometric titrations were performed analogously to standard titrations (as described in Example 5B), using reaction mixtures containing 0.6-2.6 μM (CAP-$His_6$)-$DNA^F$ [prepared by equilibration of $DNA^F$ with excess CAP-$His_6$ for 20 min. at 25° C., followed by removal of unbound CAP-$His_6$ by filtration through Bio-Rex 70 (Bio-Rad),according to methods described in Kapanidis, A. N., et al., *J. Mol. Biol.* 312:453-468 (2001)], and titrating with 0-12 μM of ($Ni^{2+}$-$NTA$)$_2$-Cy3 or ($Ni^{2+}$-$NTA$)$_2$-Cy5 by successive addition of 0.3-1.2 μl aliquots of μM ($Ni^{2+}$-$NTA$)$_2$-Cy3 or ($Ni^{2+}$-$NTA$)$_2$-Cy5. Fluorescence emission intensities were corrected for dilution and background, and values of E were corrected for non-specific interactions (by subtraction of values of E for control reaction mixtures omitting CAP-$His_6$). Corrected values of E were plotted as $E/E_{sat}$ vs. titrant concentration where $E_{sat}$ is the E at saturating titrant concentrations.

Figure 7:
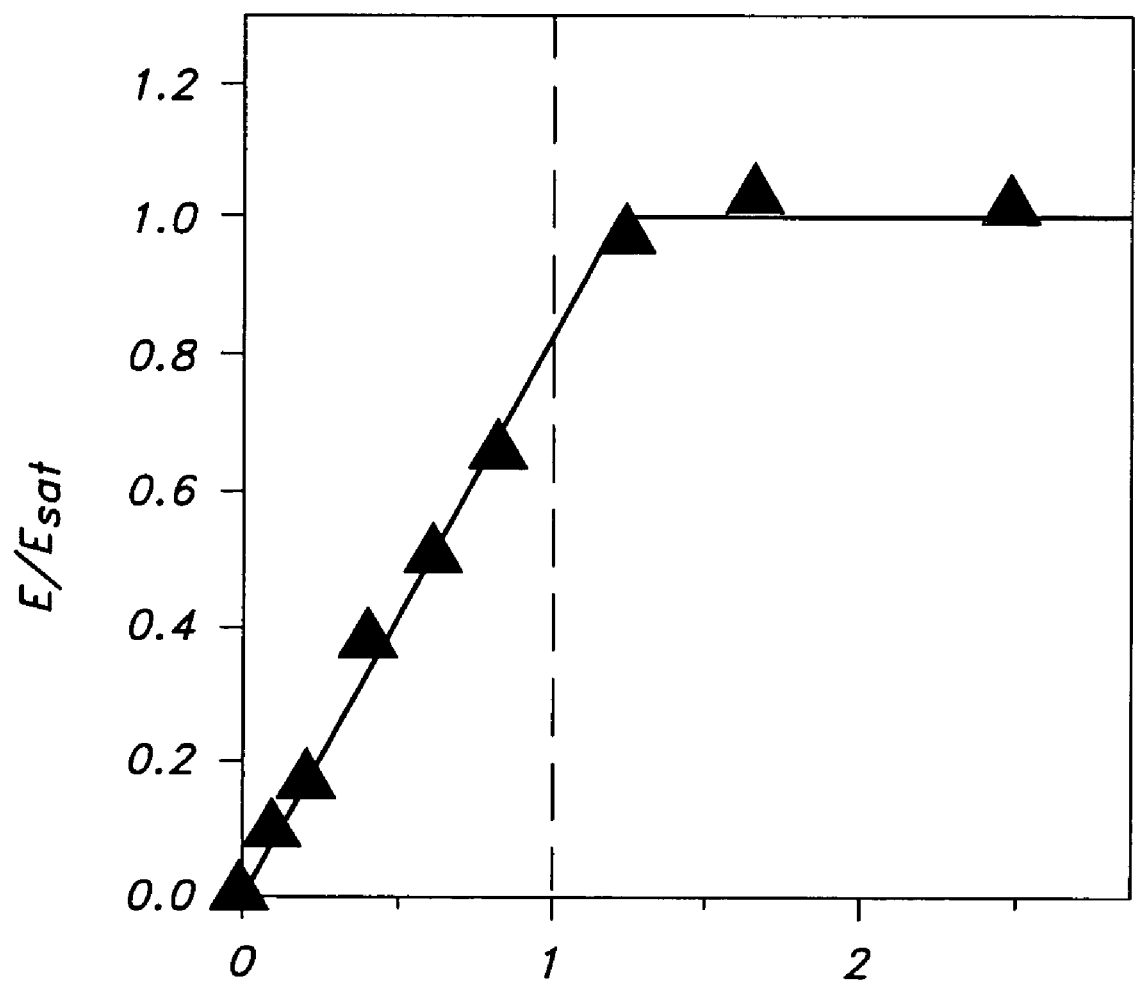
FIGS. 7 and 8 show results of FRET experiments verifying stoichiometric interactions of nickel containing probes according to the present invention with the hexahistidine tag.

Referring now to FIG. 7, a graphical representation of results of stoichiometric titration of the (CAP-$His_6$)-$DNA^F$ complex with ($Ni^{2+}$-$NTA$)$_2$-Cy5 is shown (filled circles). The interaction between with ($Ni^{2+}$-$NTA$)$_2$-Cy5 and $His_6$ has a stoichiometry is 1:1, as evidenced inflection of the titration curve at a ratio of 1 mole ($Ni^{2+}$-$NTA$)$_2$-Cy5 to 1 mole CAP-$His_6$ protomer.

Figure 8:
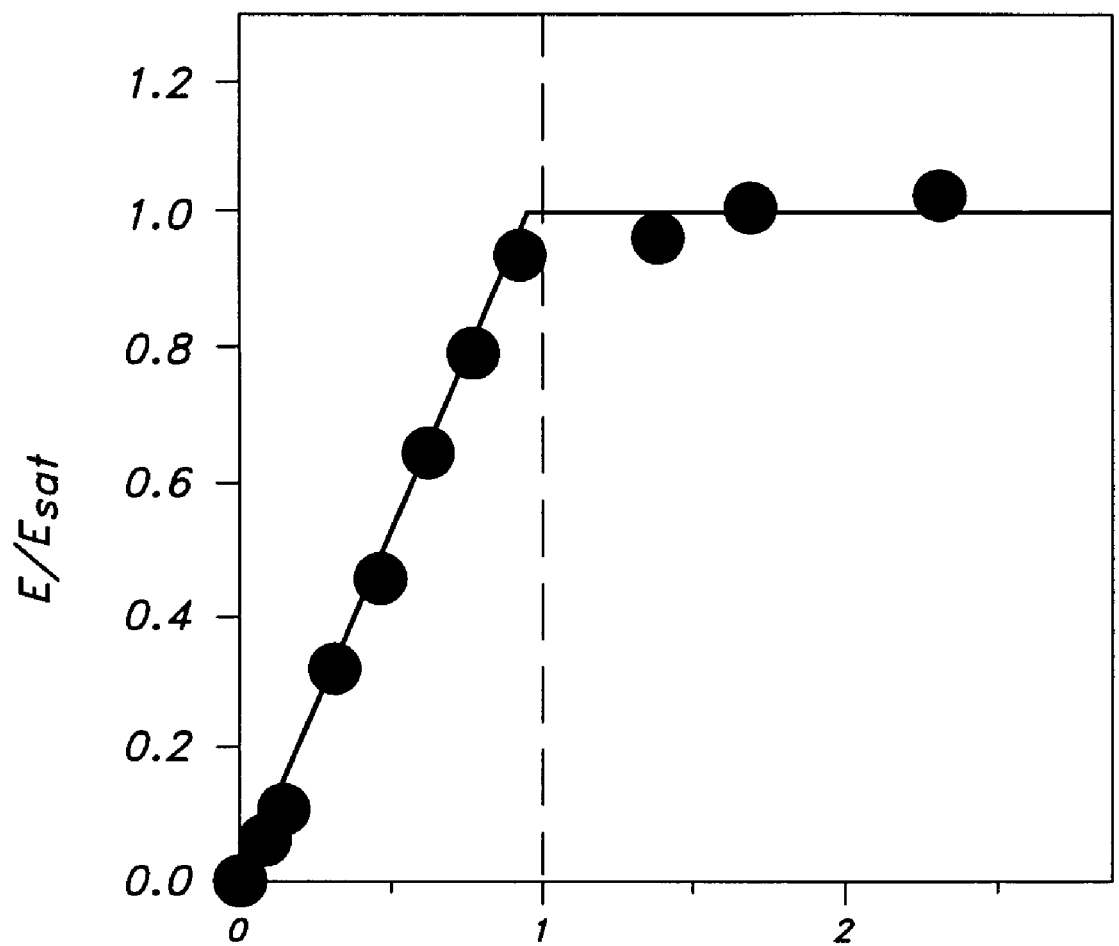

Referring now to FIG. 8, a graphical representation of results of stoichiometric titration of the (CAP-$His_6$)-$DNA^F$ complex with ($Ni^{2+}$-$NTA$)$_2$-Cy3 is shown (filled circles). The interaction between with ($Ni^{2+}$-$NTA$)$_2$-Cy3 and $His_6$ has a stoichiometry is 1:1, as evidenced inflection of the titration curve at a ratio of 1 mole ($Ni^{2+}$-$NTA$)$_2$-Cy3 to 1 mole CAP-$His_6$ protomer.

D. FRET Assays-Distance Determinations

Donor-acceptor distances, R, were determined using the measured efficiencies of FRET at saturation, $E_{sat}$ (0.45 for titration with ($Ni^{2+}$-$NTA$)$_2$-Cy5; 0.25 for titration ($Ni^{2+}$-$NTA$)$_2$-Cy5; see FIGS. 5, 6), and the measured Förster parameters, $R_0$:

$$E=R_0^6/(R_0^6+R^6)$$

$$R_0 \text{ (in Å)}=(0.211\times10^{-5})(n^{-4}Q_D\kappa^2 J)^{1/6}$$

where n is the refractive index of the medium (1.4 for dilute protein solutions[8]), $Q_D$ is the donor quantum yield in the absence of acceptor [0.4; measured using quinine sulfate in 0.1 N $N_2SO_4$ as standard ($Q_{QS}$=0.51)], $\kappa^2$ is the orientation factor relating the donor emission dipole and acceptor dipole [approximated as ⅔ due to the low fluorescent anisotropy of the donor], and J is the spectral overlap integral of the donor emission spectrum and the acceptor excitation spectrum:

$$J=[\int F_D(\lambda)\epsilon_A(\lambda)\lambda^4 d\lambda]/[\int F_D(\lambda)d\lambda]$$

where $F_D(\lambda)$ is the normalized corrected emission spectrum of donor, $\epsilon_A(\lambda)$ is the molar extinction coefficient of acceptor, and $\lambda$ is the wavelength.

Figure 4:
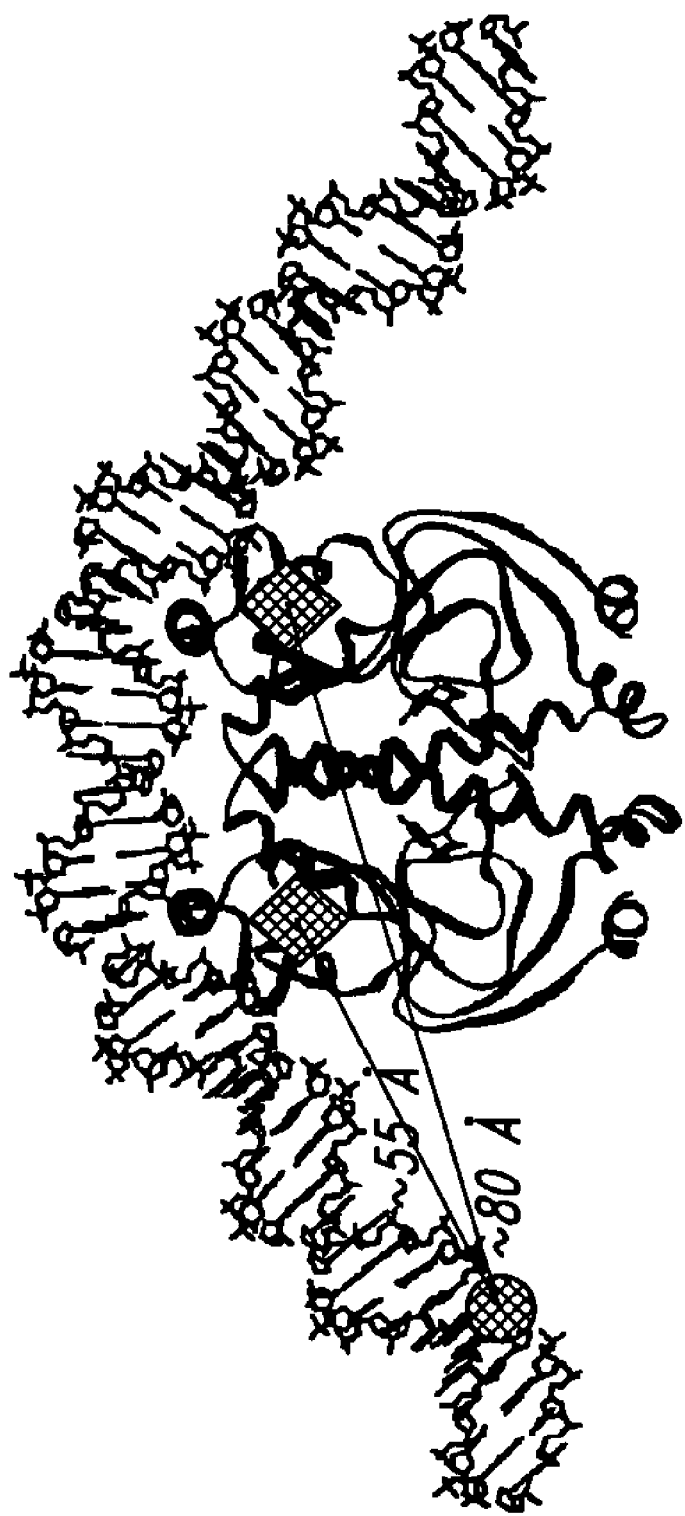
FIG. 4 is a model structure of a $DNA^F$-CAP-$His_6$ complex showing the position of the fluorescein of $DNA^F$ (circle), the position of the hexahistidine tag of each CAP-$His_6$ protomotor (diamond), the distance between fluorescein and the hexahistidine tag of the proximal CAP-$His_6$ protomotor (~55 Å), and the distance between fluorescein and the hexahistidine tag of the distal CAP-$His_6$ protomotor (~80 Å).

The analysis above yields donor-acceptor distances of 58 Å using ($Ni^{2+}$-$NTA$)$_2$-Cy3; FIG. 5) and 53 Å (using ($Ni^{2+}$-$NTA$)$_2$-Cy5; FIG. 6). The distance of 56(±) Å determined in this manner is in excellent agreement with the distance of about 55 Å expected based on structural information as illustrated in FIG. 4 (corresponding to the distance between the fluorescein on DNA and the $His_6$ of the proximal CAP-$His_6$ protomer).

The invention illustratively described herein suitably may be practiced in the absence of any element or elements, limitation or limitations, which is not specifically disclosed herein. The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed herein, optional features, modification and variation of the concepts herein disclosed may be resorted to by those skilled in the art, and that such modifications and variations are considered to be within the scope of this invention as defined by the appended claims. In addition, where features or aspects of the invention are described in terms of Markush groups, those skilled in the art will recognize that the invention is also thereby described in terms of any individual member or subgroup of members of the Markush group.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other aspects of the invention are within the following claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

We claim:

1. A method for detecting one or more molecules that include a target sequence, wherein said target sequence comprises an amino acid sequence of the form $(H)_i$, wherein H is histidine and i is an integer of from 4 to 12, said method comprising:

(a) providing a sample that comprises one or more target material, wherein said target material includes molecules having a target sequence, (b) subjecting said target material to electrophoresis in an electrophoretic medium;

(c) contacting said electrophoretic medium with at least one molecule having the general structural Formula (I), and tautomers, salts and acids thereof:

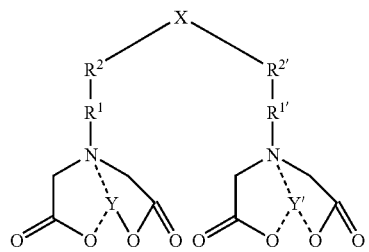

(I)

wherein the contacting is under conditions sufficient to permit transition-metal-chelate moieties of said molecule of Formula (I) to associate with said target sequence, and wherein the electrophoretic medium is contacted with the at least one molecule of Formula (I) in a solution having an alkaline pH; and (d) detecting said detectable group of the molecule of Formula (I), thereby detecting said one or more molecules that include a target sequence.

2. The method of claim 1, wherein said electrophoresis is selected from the group consisting of solution electrophoresis, SDS-PAGE, IEF, IPG electrophoresis, and 2D electrophoresis.

3. A solution for staining target molecules in an electrophoretic medium, said solution having an alkaline pH and comprising one or more molecules according to Formula (I), and tautomers, salts and acids thereof:

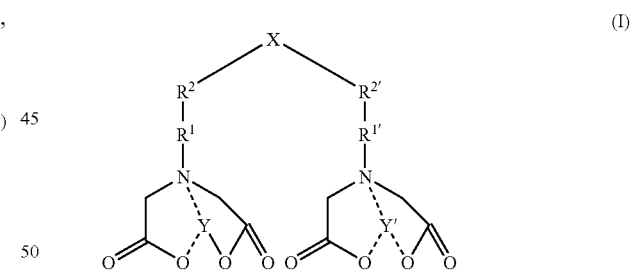

(I)

wherein (a) Y and Y' are each a transition metal; (b) $R^1$ and $R^{1'}$ are each independently CH(COO⁻), CH(COOH), or absent; (c) $R^2$ and $R^{2'}$ are linear or branched, optionally substituted, linkers of from about 3.0 to about 20 Å long; and (d) X is a detectable group; wherein said one or more molecules according to Formula (I) are present in a concentration sufficient to stain molecules including a target sequence in an electrophoretic medium, said target sequence comprising an amino acid sequence of the form $(H)_i$, wherein H is histidine and i is an integer of from 4 to 12.

4. The method of claim 1, wherein the electrophoretic medium is contacted with the at least one molecule according to Formula (I) in a solution having a pH of between 7.1 and 8.0.

wherein (a) Y and Y' are each a transition metal; (b) $R^1$ and $R^{1'}$ are each independently CH(COO⁻), CH(COOH), or absent; (c) $R^2$ and $R^{2'}$ are linear or branched, optionally substituted, linkers of from about 3.0 to about 20 Å long; and (d) X is a detectable group;

5. The method of claim 1, wherein the electrophoretic medium is contacted with the at least one molecule according to Formula (I) in a solution having a pH of between 7.6 and 8.2.

6. The method of claim 1, wherein the electrophoretic medium is contacted with the at least one molecule according to Formula (I) in a solution having a pH of between 7.6 and 8.0.

7. The method of claim 4, wherein the at least one molecule according to Formula (I) is present at a concentration from 0.05 μM to 1 μM.

8. The method of claim 4, wherein said solution further comprises a preservative.

9. The method of claim 4, wherein said solution further comprises a phosphate buffer or a Tris buffer.

10. The method of claim 1, wherein the electrophoretic medium is contacted with the at least one molecule according to Formula (I) in a solution comprising a phosphate buffer.

11. The method of claim 4, wherein said solution further comprises a metal ion salt.

12. The solution of claim 3, wherein the solution has a pH of between 7.1 and 8.0.

13. The solution of claim 3, wherein the solution has a pH of between 7.6 and 8.2.

14. The solution of claim 3, wherein the solution has a pH of between 7.6 and 8.0.

15. The solution of claim 12, wherein the at least one molecule according to Formula (I) is present at a concentration from 0.05 μM to 1 μM.

16. The solution of claim 12, further comprising a preservative.

17. The solution of claim 12, further comprising a phosphate buffer or a Tris buffer.

18. The solution of claim 3, wherein the solution comprises a phosphate buffer.

19. The solution of claim 12, further comprising a metal ion salt.

20. The solution of claim 12, wherein the solution is present in a ready-to-use form in a container.

* * * * *